US007894872B2

(12) United States Patent
Sherman

(10) Patent No.: US 7,894,872 B2
(45) Date of Patent: Feb. 22, 2011

(54) COMPUTER ASSISTED ORTHOPAEDIC SURGERY SYSTEM WITH LIGHT SOURCE AND ASSOCIATED METHOD

(75) Inventor: Jason T. Sherman, Leesburg, IN (US)

(73) Assignee: DePuy Orthopaedics, Inc, Warsaw, IN (US)

( * ) Notice: Subject to any disclaimer, the term of this patent is extended or adjusted under 35 U.S.C. 154(b) by 1336 days.

(21) Appl. No.: 11/319,817

(22) Filed: Dec. 26, 2005

(65) Prior Publication Data
US 2007/0167701 A1    Jul. 19, 2007

(51) Int. Cl.
A61B 5/00    (2006.01)
(52) U.S. Cl. ..................................... 600/407
(58) Field of Classification Search ................ 600/407, 600/424, 476
See application file for complete search history.

(56) References Cited

U.S. PATENT DOCUMENTS

| 2,990,765 | A | 4/1961 | Winzenburg |
| 5,650,817 | A | 7/1997 | Jae-chon |
| 5,954,648 | A | 9/1999 | Van Der Brug |
| 5,973,728 | A | 10/1999 | Levitan |
| 6,715,904 | B2* | 4/2004 | Naughton ................... 362/399 |

FOREIGN PATENT DOCUMENTS

| EP | 0 672 389 | 9/1995 |
| WO | 99/274839 | 6/1999 |

OTHER PUBLICATIONS http://www.z-bolt.com, "Z-Bolt.com Beam of Light Technologies", Printed from website on Nov. 23, 2005, 1 page.

* cited by examiner

Primary Examiner—Brian Casler
Assistant Examiner—Jonathan G Cwern
(74) Attorney, Agent, or Firm—Barnes & Thornburg LLP

(57) ABSTRACT

A computer assisted orthopaedic surgery system comprises an image sensor and a light source. The image sensor is configured to sense an image of an area associated with an orthopaedic surgical site and has a field of view. The light source projects light distinct from any ambient lighting onto the area in a pattern visually indicative of at least a portion of the field of view. An associated method is disclosed.

20 Claims, 22 Drawing Sheets

COMPUTER ASSISTED ORTHOPAEDIC SURGERY SYSTEM WITH LIGHT SOURCE AND ASSOCIATED METHOD

TECHNICAL FIELD

The present disclosure relates generally to computer assisted orthopaedic surgery systems.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation. CAOS systems assist surgeons in the performance of orthopaedic surgical procedures by, for example, displaying images illustrating surgical steps of the surgical procedure being performed. Typical CAOS systems are stand-alone systems that are neither integrated with, nor configured to communicate with, other electronic systems or networks such as, for example, hospital networks. As such, typical CAOS systems are unable to access electronic data, such as medical records and the like, stored in the other electronic systems and networks.

SUMMARY

A computer assisted orthopaedic surgery system comprises an image sensor and a light source. The image sensor is configured to sense an image of an area associated with an orthopaedic surgical site and has a field of view. The light source is secured to the image sensor to project light distinct from any ambient lighting onto the area in a pattern visually indicative of at least a portion of the field of view. Such an arrangement facilitates repositioning of the image sensor so that a desired portion of the area can be placed within the field of view for display in a relatively quick and efficient manner. An associated method is disclosed.

Illustratively, the light source projects light onto the area in a linear pattern. The linear pattern may take the form of a wide variety of shapes and sizes including, but not limited to, a circle, an ellipse, a rectangle, a triangle, a polygon, any other geometric shape, or an irregular shape, to name just a few. The lines of the linear pattern may be solid or broken. The image sensor may thus be repositioned so that the desired portion of the area is within the boundaries of the linear pattern to thereby indicate to a user of the computer assisted orthopaedic system that the desired portion is within the field of view.

Exemplarily, the light source includes a light generator and an optical device. The light source generates light which is modified by the optical device into the desired pattern (linear or otherwise). The light generator may take the form of, for example, a laser, a laser diode, an incandescent, a fluorescent light, or the like. The optical device may include, but is not limited to, lenses, mirrors, fiber optics, and the like.

The light source may be used with a variety of image sensors. For example, the image sensor may be a stereoscopic camera head having two cameras arranged in stereoscopic relation or it may have only a single camera.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

Figure 1:
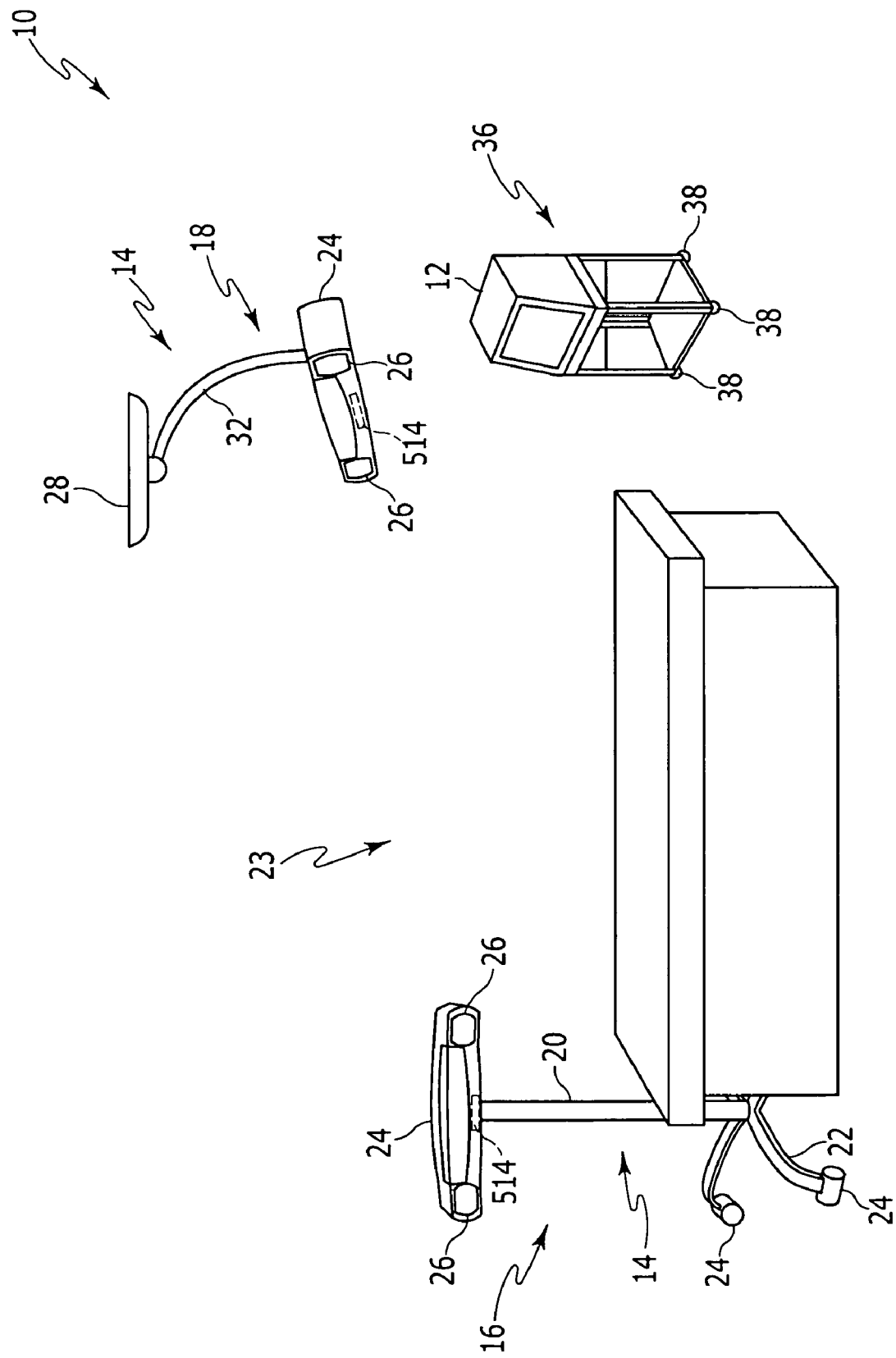
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as a Ci™ system commercially available from DePuy Orthopaedics, Inc. of Warsaw, Ind. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 24 to allow the mobile camera unit 16 to be repositioned within a hospital room 23. The mobile camera unit 16 includes an image sensor 24 embodied as a camera head. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 24, and an arm 32 coupling the camera head 24 with the base 28. In some embodiments, other peripherals, such as display screens, lights, and the like, may also be coupled with the base 28. The camera head 24 includes two cameras 26. The fixed camera unit 18 may be coupled to a ceiling, as illustratively shown in FIG. 1, or a wall of the hospital room. Similar to the camera head 24 of the mobile camera unit 16, the camera head 24 of the fixed camera unit 18 may be positionable relative to the arm 32 such that the field of view of the cameras 26 of the fixed camera unit 18 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
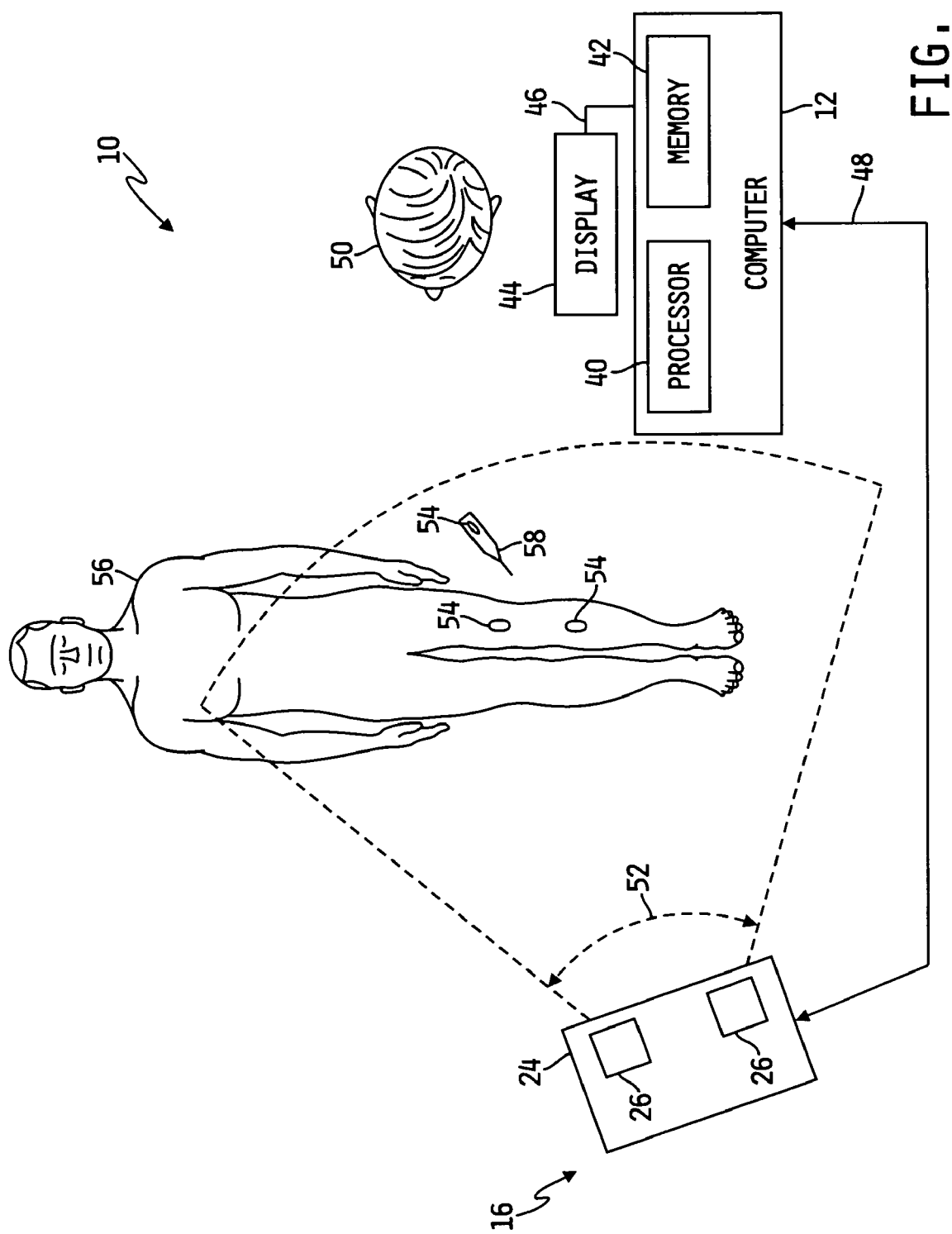
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
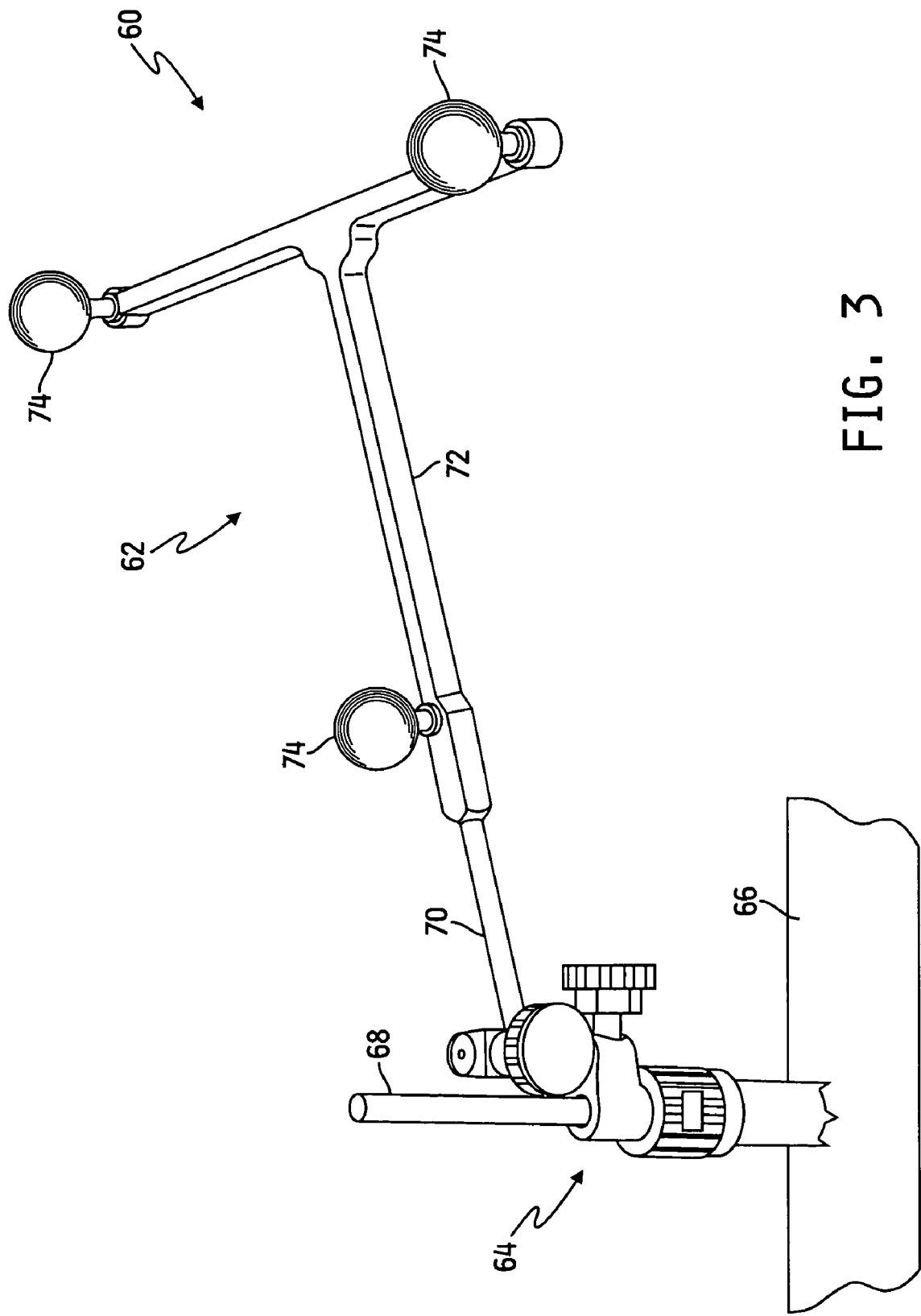
FIG. 3 is a perspective view of a bone locator tool.

The CAOS system 10 may also include a number of sensors or sensor arrays 54 which may be coupled the relevant bones of a patient 56 and/or with orthopaedic surgical tools 58. For example, as illustrated in FIG. 3, a tibial array 60 includes a sensor array 62 and bone clamp 64. The illustrative bone clamp 64 is configured to be coupled with a tibia bone 66 of the patient 56 using a Schantz pin 68, but other types of bone clamps may be used. The sensor array 62 is coupled with the bone clamp 64 via an extension arm 70. The sensor array 62 includes a frame 72 and three reflective elements or sensors 74. The reflective elements 74 are embodied as spheres in the illustrative embodiment, but may have other geometric shapes in other embodiments. Additionally, in other embodiments sensor arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
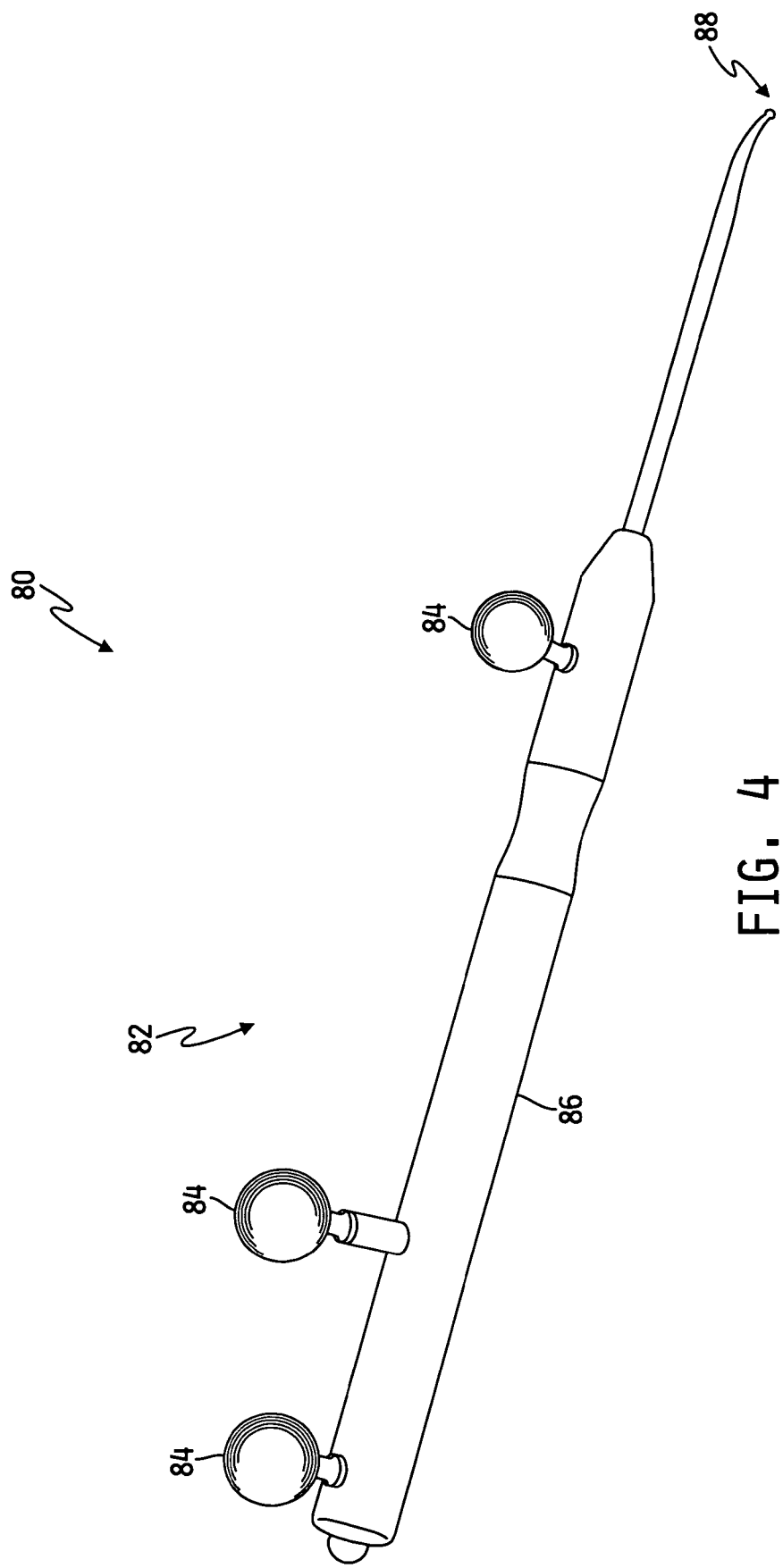
FIG. 4 is a perspective view of a registration tool for use with the system of FIG. 1.
Figure 5:
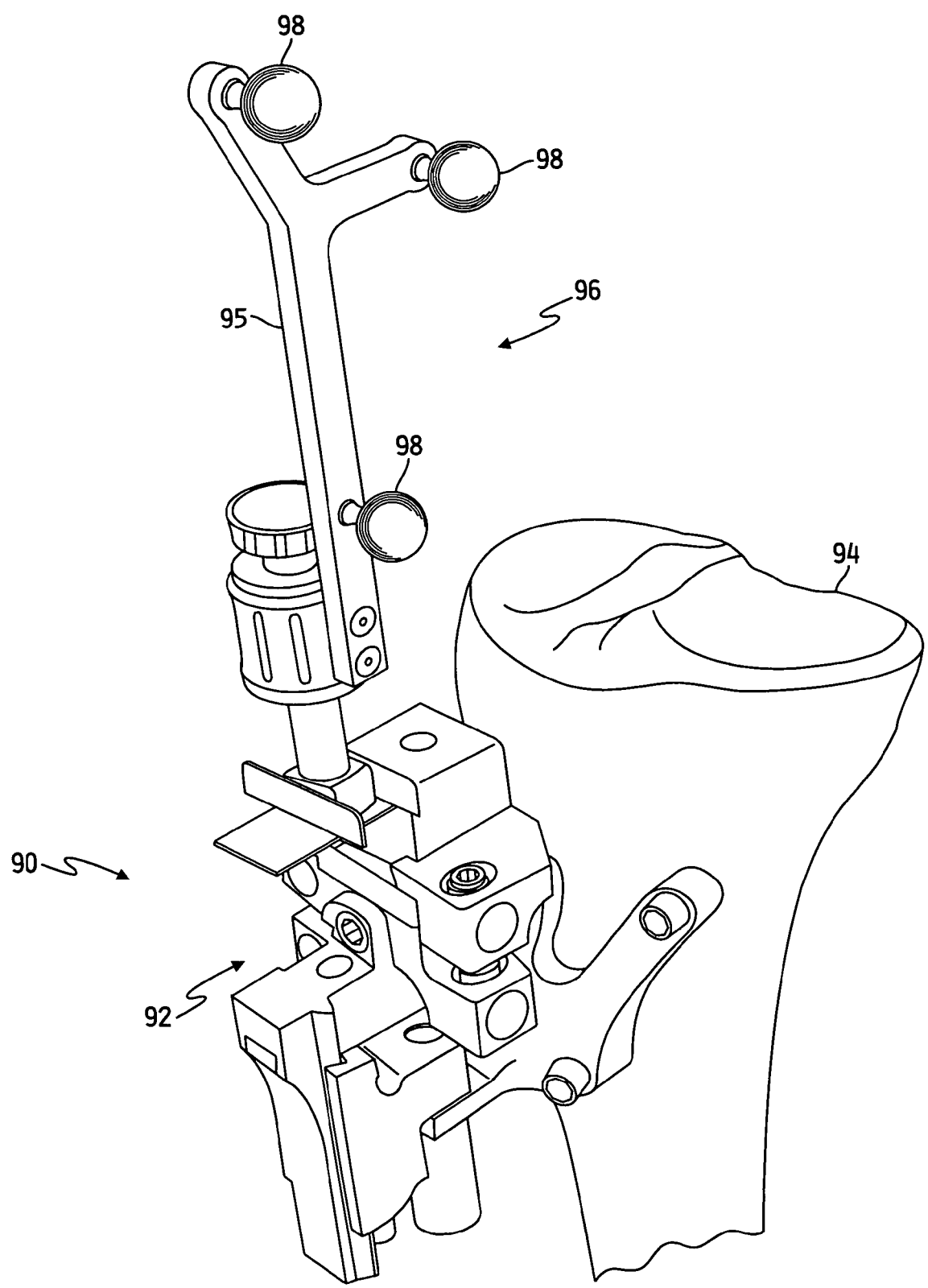
FIG. 5 is a perspective view of an orthopaedic surgical tool for use with the system of FIG. 1.
Figure 7:
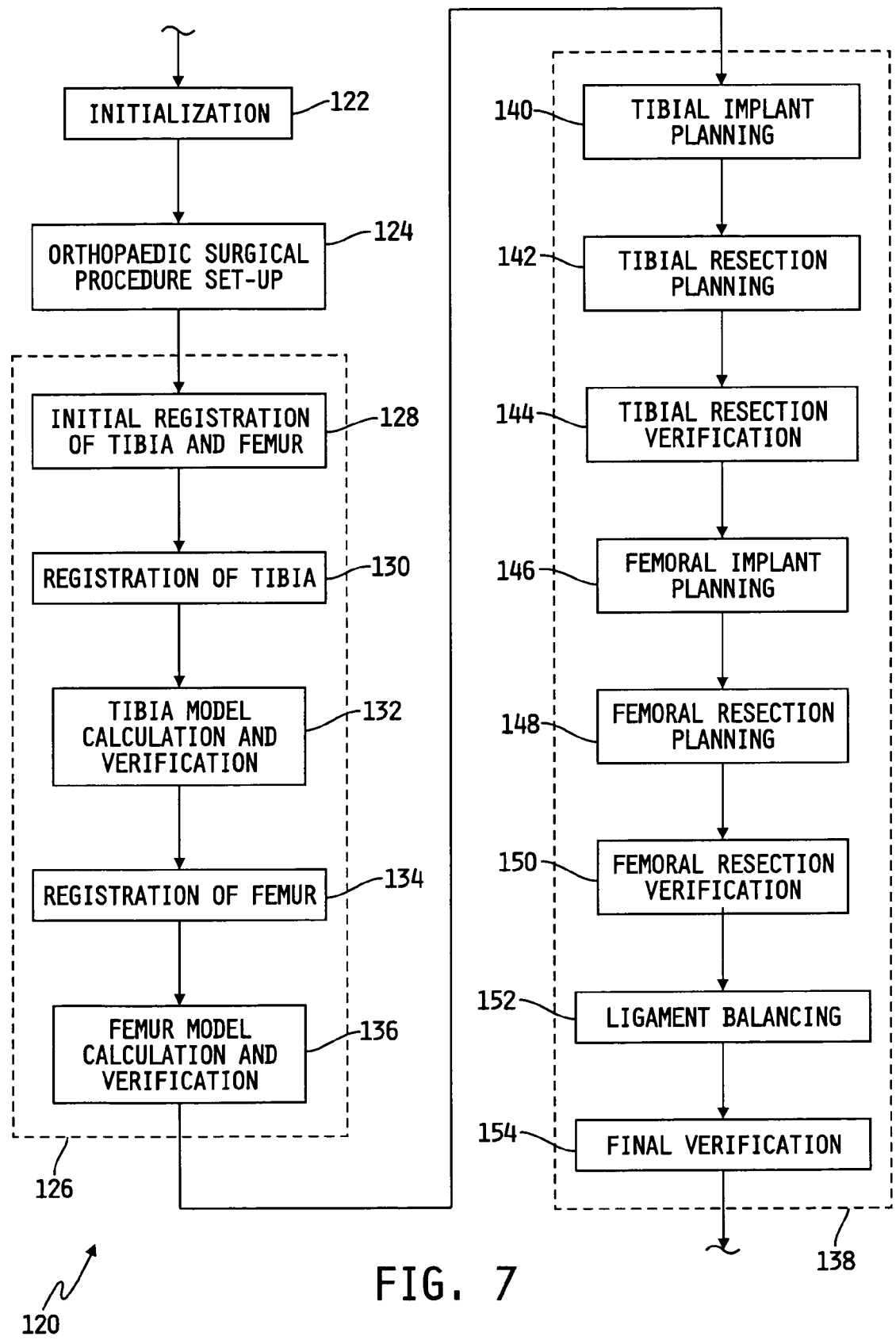
FIG. 7 is a simplified flowchart diagram of one particular embodiment of the algorithm of FIG. 6.

Sensor arrays may also be coupled to other surgical tools. For example, a registration tool 80, as shown in FIG. 4, is used to register points of a bone as discussed in more detail below in regard to FIG. 7. The registration tool 80 includes a sensor array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, sensor arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a sensor array 96 that is coupled with the portion 92 via a frame 95. The sensor array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walk-through" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the sensor arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
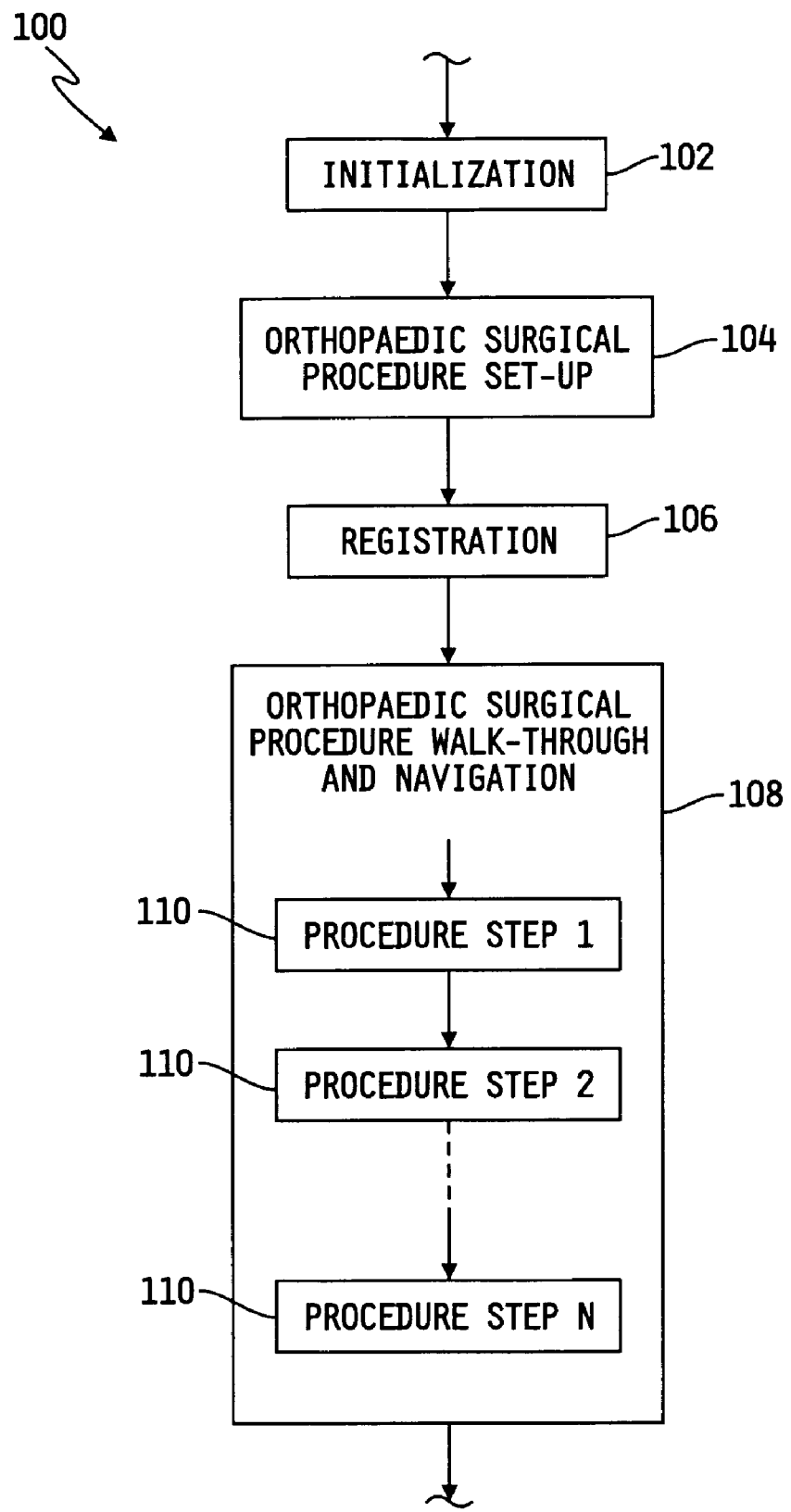
FIG. 6 is a simplified flowchart diagram of an algorithm that is used by the CAOS system of FIG. 1.

Referring now to FIG. 6, an algorithm 100 for assisting a surgeon in performing an orthopaedic surgical procedure is executed by the computer 12. The algorithm 100 begins with a process step 102 in which the CAOS system 10 is initialized. During process step 102, settings, preferences, and calibrations of the CAOS system 10 are established and performed. For example, the video settings of the display device 44 may be selected, the language displayed by the computer 12 may be chosen, and the touch screen of the display device 44 may be calibrated in process step 102.

In process step 104, the selections and preferences of the orthopaedic surgical procedure are chosen by the surgeon. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in process step 104, the bones of the patient are registered in process step 106. To do so, sensor arrays, such as the tibial array 60 illustrated in FIG. 3, are coupled with the relevant bones of the patient (i.e., the bones involved in the orthopaedic surgical procedure). Additionally, the contours of such bones are registered using the registration tool 80. To do so, the pointer end 88 of the tool 80 is touched to various areas of the bones to be registered. In response to the registration, the computer 12 displays rendered images of the bones wherein the location and orientation of the bones are determined based on the sensor arrays coupled therewith and the contours of the bones are determined based on the registered points. Because only a selection of the points of the bone is registered, the computer 12 calculates and renders the remaining areas of the bones that are not registered with the tool 80.

Figure 8:
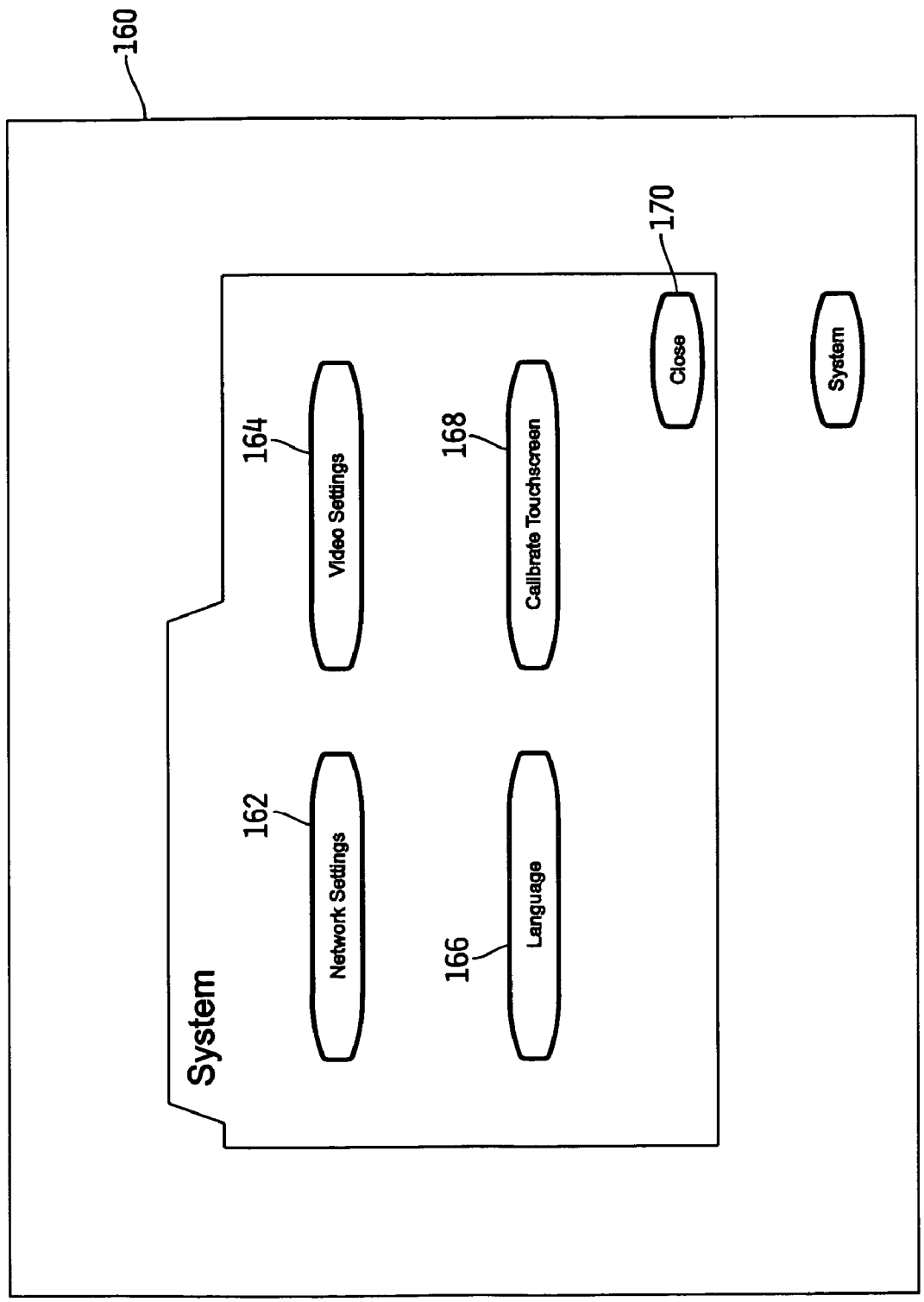
FIGS. 8-17 illustrate various screen images that are displayed to a surgeon during the operation of the system of FIG. 1.

Once the pertinent bones have been registered in process step 106, the computer 12, in cooperation with the camera unit 16, 18, displays the images of the surgical steps of the orthopaedic surgical procedure and associated navigation data (e.g., location of surgical tools) in process step 108. To do so, the process step 108 includes a number of sub-steps 110 in which each surgical procedure step is displayed to the surgeon 50 in sequential order along with the associated navigational data. The particular sub-steps 110 that are displayed to the surgeon 50 may depend on the selections made by the surgeon 50 in the process step 104. For example, if the surgeon 50 opted to perform a particular procedure tibia-first, the sub-steps 110 are presented to the surgeon 50 in a tibia-first order Referring now to FIG. 7, in one particular embodiment, an algorithm 120 for assisting a surgeon in performing a total knee arthroplasty procedure may be executed by the computer 12. The algorithm 120 includes a process step 122 in which the CAOS system 10 is initialized. The process step 122 is similar to the process step 102 of the algorithm 100 described above in regard to FIG. 6. In process step 122, the preferences of the CAOS system 10 are selected and calibrations are set. To do so, the computer 12 displays a user initialization interface 160 to the surgeon 50 via the display device 44 as illustrated in FIG. 8. The surgeon 50 may interact with the interface 160 to select various initialization options of the CAOS system 10. For example, the surgeon 50 may select a network settings button 162 to change the network settings of the system 10, a video settings button 164 to change the video settings of the system 10, a language button 166 to change the language used by the system 10, and/or a calibration button 168 to change the calibrations of the touch screen of the display device 44. The surgeon 50 may select a button by, for example, touching an appropriate area of the touch screen of the display device 44, operating an input device such as a mouse to select the desired on-screen button, or the like.

Additional images and/or screen displays may be displayed to the surgeon 50 during the initialization process. For example, if the surgeon 50 selects the button 162, a network setting interface may be displayed on the device 44 to allow the surgeon 50 to select different values, connections, or other options to change the network settings. Once the CAOS system 10 has been initialized, the surgeon 50 may close the user initialization interface 160 by selecting a close button 170 and the algorithm 122 advances to the process step 124.

Figure 9:
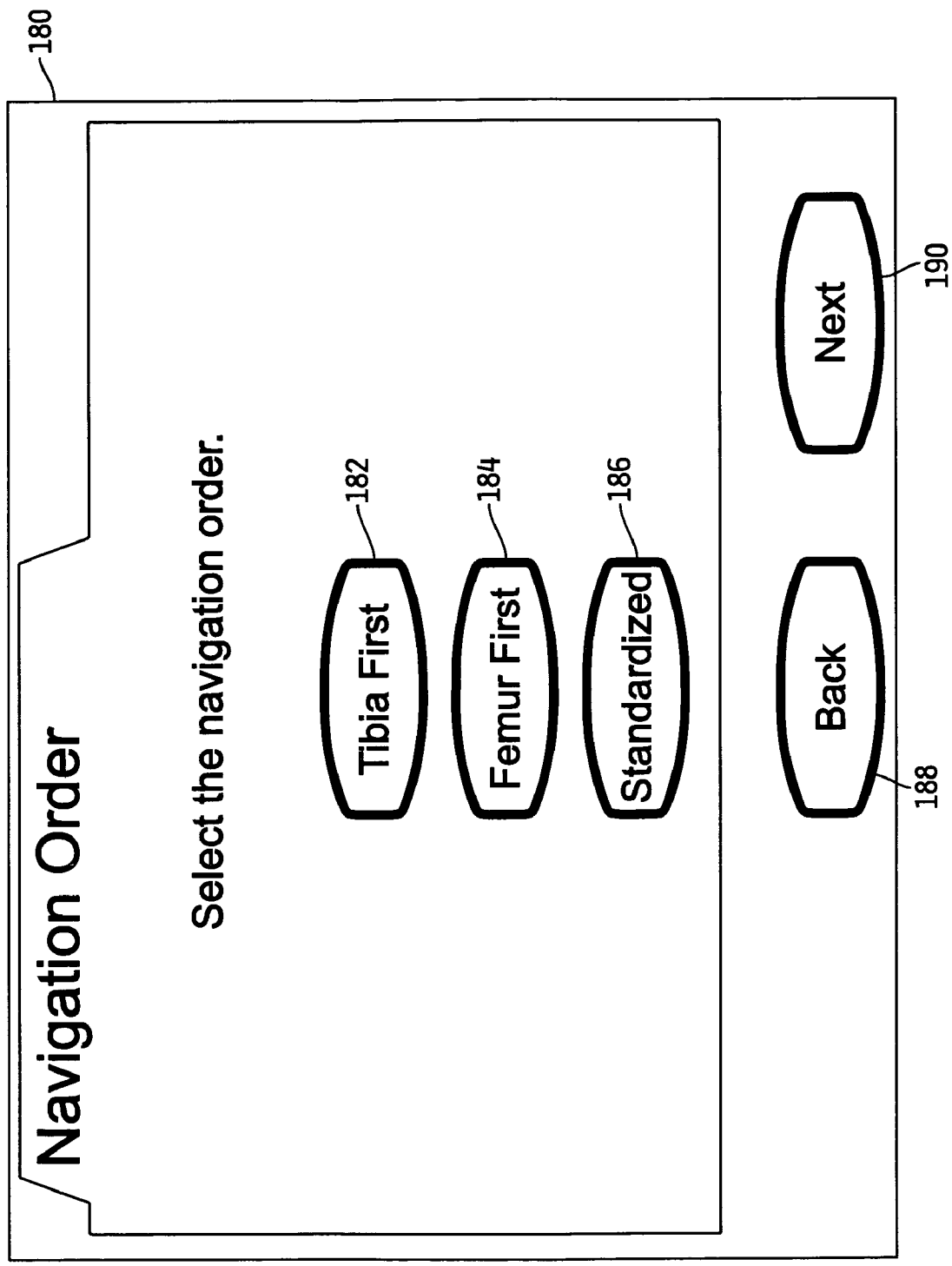

In process step 124, selections of the orthopaedic surgical procedure are chosen by the surgeon 50. The process step 124 is similar to the process step 104 of the algorithm 100 described above in regard to FIG. 6. For example, the selections made in the process step 104 may include, but are not limited to, the type of orthopaedic surgical procedure that is to be performed, the type of orthopaedic implant that will be used, and the sequence of operation, and the like. To do so, a number of procedure preference selection screens may be displayed to the surgeon 50 via the display device 44. For example, as illustrated in FIG. 9, a navigation order selection screen 180 may be displayed to the surgeon 50. The surgeon 50 may interact with the screen 180 to select the navigational (i.e., surgical) order of the orthopaedic surgical procedure being performed (i.e., a total knee arthroplasty procedure in the illustrative embodiment). For example, the surgeon 50 may select a button 182 to instruct the controller 12 that the tibia bone of the patient 56 will be operated on first, a button 184 to instruct the controller 12 that the femur bone will be operated on first, or a button 186 to select a standardized navigation order based on, for example, the type of orthopaedic implant being used. The surgeon 50 may also navigate among the selection screens by a back button 188 to review previously displayed orthopaedic surgical procedure set-up screens or a next button 190 to proceed to the next orthopaedic surgical procedure set-up screen. Once the surgeon 50 has selected the appropriate navigation order and/or other preferences and settings of the orthopaedic surgical procedure being performed, the algorithm 120 advances to the process step 126.

In the process step 126, the relevant bones of the patient 56 are registered. The process step 126 is similar to the registration process step 106 of the algorithm 100. The process step 126 includes a number of sub-steps 128-136 in which the bones of the patient 56 involved in the orthopaedic surgical procedure are registered. In process step 128, the relevant bones are initially registered. That is, in the illustrative algorithm 120, a tibia and a femur bone of the patient 56 are initially registered. To do so, a tibia array, such as the tibia array 60 illustrated in and described above in regard to FIG. 3, and a femur array are coupled with the respective bones. The tibia and femur arrays are coupled in the manner described above in regard to the tibia array 60. The camera head 24 of the camera unit 16 is adjusted such that the tibia and femur arrays are within the field of view 52 of the camera head 24. Once the arrays are coupled and the camera head 24 properly positioned, the tibia and femur of the patient 56 are initially registered.

Figure 10:
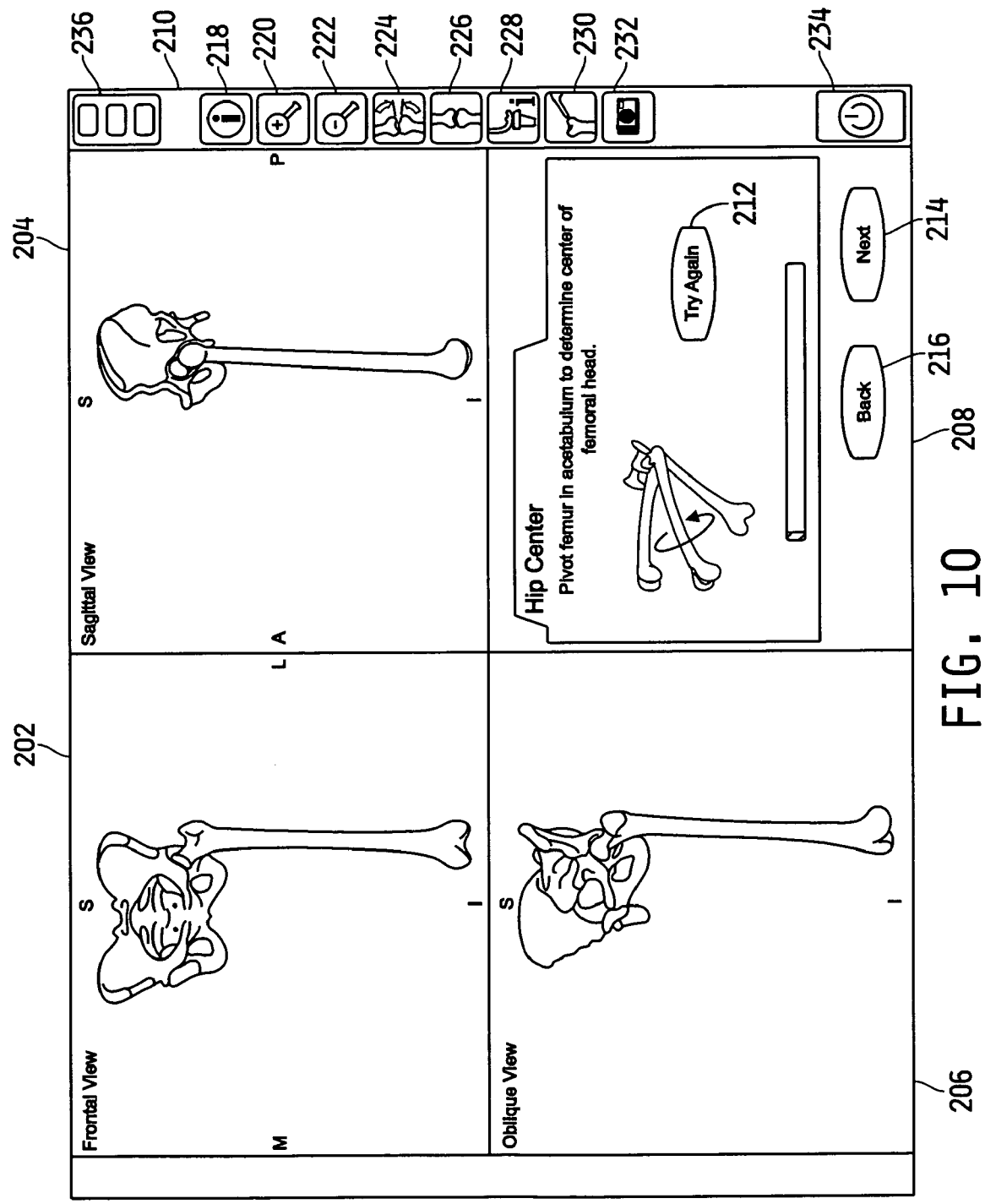

To do so, the controller 12 displays a user interface 200 to the surgeon 50 via the display device 44, as shown in FIG. 10. The interface 200 includes several navigation panes 202, 204, 206, a surgical step pane 208, and a tool bar 210. Navigational data is displayed to the surgeon 50 in the navigation panes 202, 204, 206. The computer 12 displays different views of the bone and/or surgical tools 58 in each of the panes 202, 204, 206. For example, a frontal view of the patient's 56 hip and femur bone is displayed in the navigation pane 202, a sagittal view of the patient's 56 bones is displayed in the navigation pane 204, and an oblique view of the patient's 56 bones is displayed in the navigation pane 206.

The computer 12 displays the surgical procedure steps in the pane 208. For example, in FIG. 10, the computer 12 is requesting the leg of the patient 56 be moved about in a circular motion such that the femur bone of the patient 56 is initially registered. In response, the computer 12 determines the base location and orientation of the femur bone (e.g., the femur head) of the patient 56 based on the motion of the sensor array 54 coupled with the bone (i.e., based on the image data of the sensor array 54 received from the camera head 24). Although only the femur bone is illustrated in FIG. 10 as being initially registered, it should be appreciated that the tibia bone is also initially registered and that other images and display screen are displayed to the surgeon 50 during such initial registration.

The surgeon 50 can attempt to initially register the bones as many times as required by selecting a "try again" button 212. Once the relevant bones have been initially registered, the surgeon 50 can advance to the next surgical procedure step of the registration step 126 by selecting the next button 214. Alternatively, the surgeon 50 can skip one or more of the initial registration steps by selecting the button 214 and advancing to the next surgical procedure step while not performing the initial registration step (e.g., by not initially registering the femur bone of the patient 56). The surgeon 50 may also go back to the previous surgical procedure step (e.g., the initial registration of the tibia) by selecting a back button 216. In this way, the surgeon 50 can navigate through the surgical setup, registration, and procedure steps via the buttons 214, 216.

The toolbar 210 includes a number of individual buttons, which may be selected by the surgeon 50 during the performance of the orthopaedic surgical procedure. For example, the toolbar 210 includes an information button 218 that may be selected to retrieve and display information on the application software program being executed by the computer 12 such as the version number, "hotline" phone numbers, and website links. The toolbar 210 also includes zoom buttons 220 and 222. The zoom button 220 may be selected by the surgeon 50 to zoom in on the rendered images displayed in the panes 202, 204, 206 and the zoom button 222 may be used to zoom out. A ligament balancing button 224 may be selected to proceed to a ligament balancing procedure, which is described in more detail below in regard to process step 152. A 3D model button 226 may be selected to alternate between the displaying of the rendered bone (e.g., femur or tibia) and displaying only the registered points of the rendered bone in the navigation panes 202, 204, and 206. An implant information button 228 may be selected to display information related to an orthopaedic implant selected during later steps of the orthopaedic surgical procedure (e.g., process steps 140 and 146 described below). Such information may include, for example, the make, type, and size of the orthopaedic implant. A registration verification button 230 may be selected by the surgeon 50 at any time during the procedure to verify the rendered graphical model of a bone if, for example, the sensor arrays 54 coupled with the bone are accidentally bumped or otherwise moved from their fixed position. A screenshot button 232 may also be selected by the surgeon 50 at any time during the performance of the orthopaedic surgical procedure to record and store a screenshot of the images displayed to the surgeon 50 at that time. The screenshots 50 may be recorded in a storage device, such as a hard drive, of the computer 12. A close button 234 may be selected to end the current navigation and surgical procedure walk-through. After selecting the button 234, any information related to the orthopaedic surgical procedure that has been recorded, such as screenshots and other data, are stored in the storage device of the computer 12 for later retrieval and review.

The toolbar 210 also includes a status display 236. The status display 236 displays different color lights that indicate whether the system 10 can "see" or otherwise detect the sensor arrays 54 coupled with the bones and/or surgical tools. The status display 236 is also a button that may be selected to view a help screen illustrating a graphical rendering of the field of view 52 of the camera head 24 such that the positioning of the camera unit 16 and the sensor arrays 54 and surgical tools 58 can be monitored and adjusted if needed.

Figure 11:
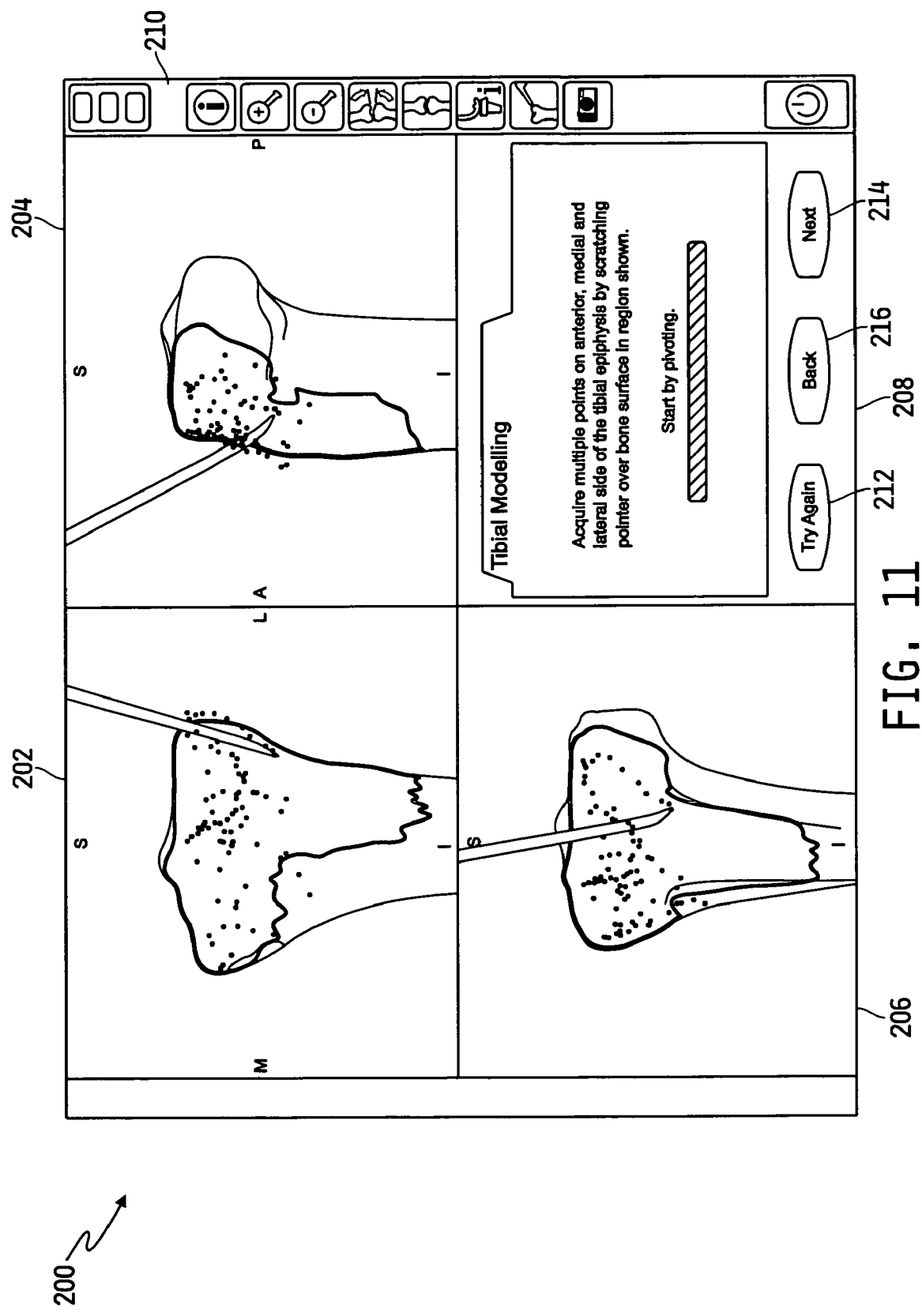

Once the initial registration of the tibia and femur bones of the patient 56 is complete, the algorithm 120 advances to process step 130 in which the contour of the proximal tibia of the patient 56 is registered. To do so, the surgeon 50 uses a registration tool, such as the registration tool 80 illustrated in and described above in regard to FIG. 4. As illustrated in FIG. 11, the surgeon 50 registers the proximal tibia by placing the pointer end 88 of the registration tool 80 on the surface of the tibia bone as instructed in the surgical step pane 208. Contour points of the tibia bone are recorded by the computer 12 periodically as the pointer end 88 is dragged across the surface of the tibia bone and/or placed in contact with the tibia bone. The surgeon 50 registers enough points on the proximal tibia such that the computer 12 can determine and display a relatively accurate rendered model of the relevant portions of the tibia bone. Portions of the tibia bone that are not registered, but rather rendered by the computer 12 based on a predetermined model of the tibia bone, are displayed to the surgeon 50 in a different color than the registered portions of the tibia bone. In this way, the surgeon 50 can monitor the registration of the tibia bone and ensure that all relevant portions of the tibia bone have been registered to improve the accuracy of the displayed model.

Once all the relevant portions of the proximal tibia have been registered in process step 130, the tibia model is calculated and verified in process step 132. To do so, the surgeon 50 follows the instructions provided in the surgical step pane

Figure 12:
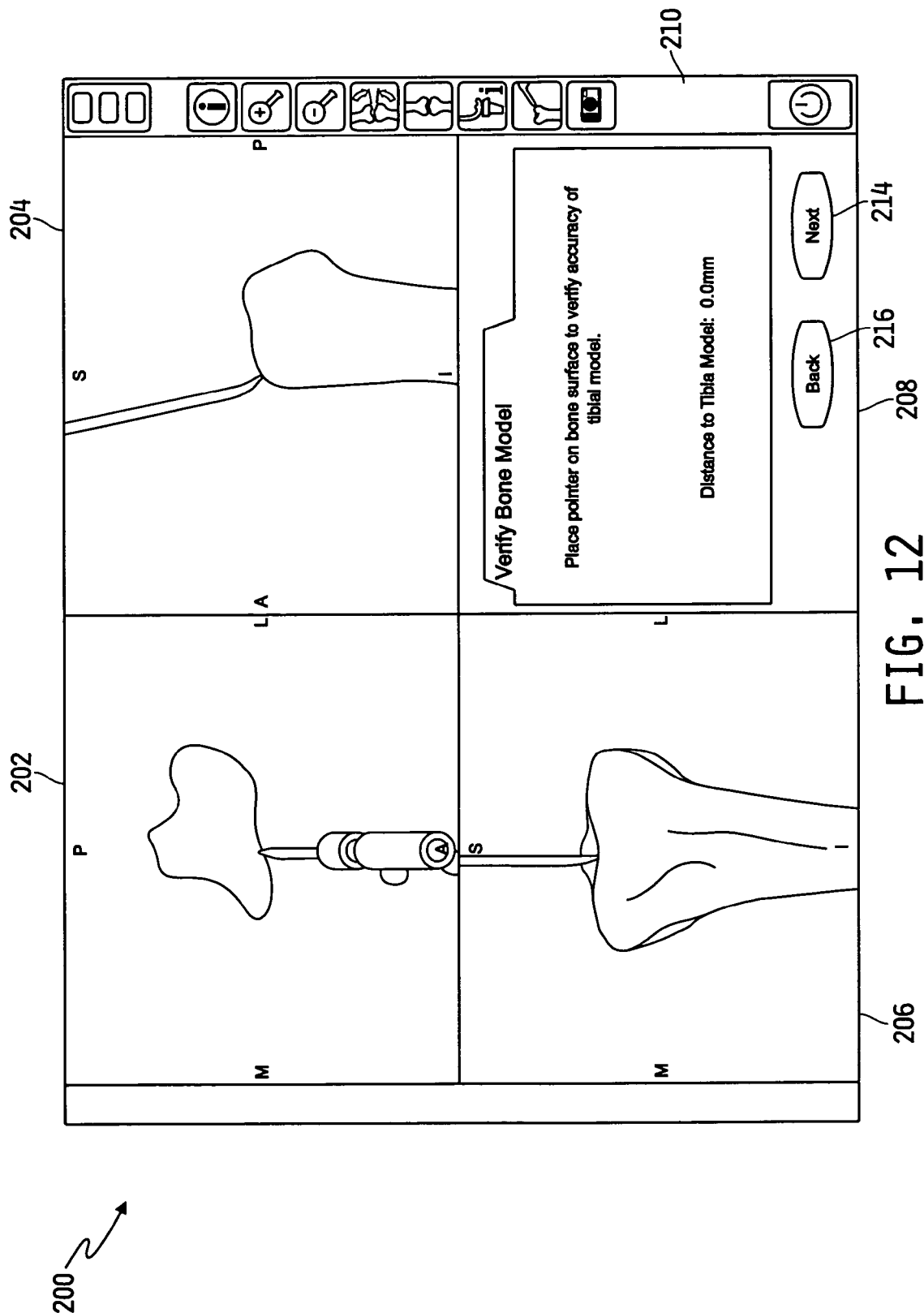

208. The proximal tibia is verified by touching the pointer end 88 of the registration tool 80 to the registered portions of the tibia bone and monitoring the distance data displayed in the pane 208 as illustrated in FIG. 12. Based on the distance data, the surgeon 50 can determine if the current tibia model is accurate enough for the orthopaedic surgical procedure. If not, the surgeon 50 can redo the registration of the proximal tibia or supplement the registration data with additional registration points by selecting the back button 216. Once the model of the patient's 56 tibia has been determined to be sufficiently accurate, the surgeon 50 may proceed by selecting the next button 214.

The distal femur of the patient 56 is registered next in the process step 134. The registration of the femur in process step 134 is similar to the registration of the tibia in the process step 130. That is, the registration tool 80 is used to registered data points on the distal femur. Once the registration of the femur is complete, the femur model is calculated and verified in process step 136. The verification of the femur in process step 136 is similar to the verification of the tibia in process step 132. The registration tool 80 may be used to touch pre-determined portions of the femur to determine the accuracy of the femur model. Based on the distance data displayed in the surgical step pane 208, the surgeon 50 may reregister the femur or add addition registration data points to the model by selecting the back button 216. Once the femur bone model is verified, the surgeon 50 can proceed with the orthopaedic surgical procedure by selecting the next button 214.

Figure 13:
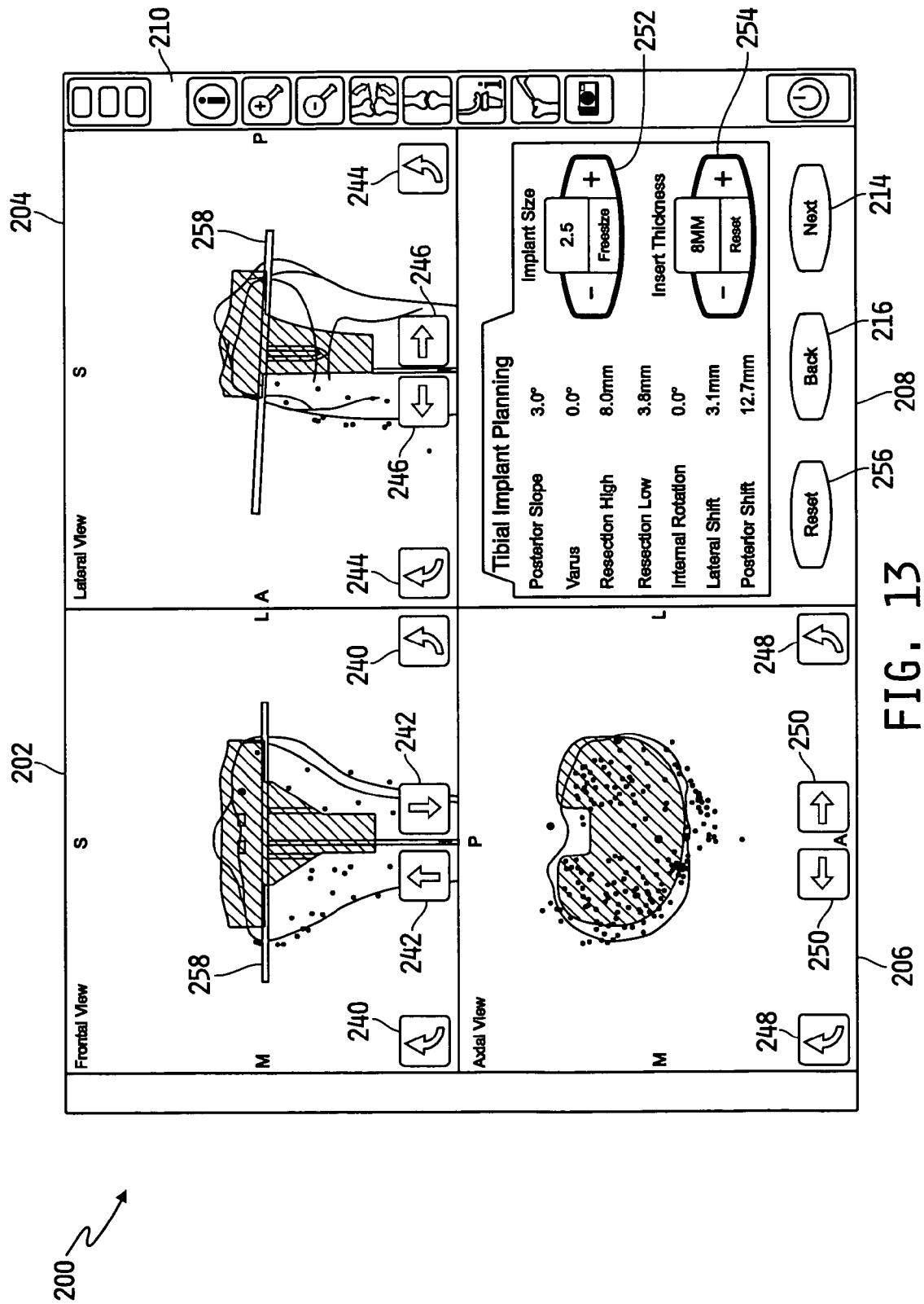

Once the relevant bones (i.e., the proximal tibia and distal femur) have been registered in process step 126, the algorithm 120 advances to process step 138 in which the computer 12 displays images of the individual surgical steps of the orthopaedic surgical procedure and the associated navigation data to the surgeon 50. To do so, the process step 138 includes a number of sub-steps 140-154. In process step 140 the planning for the tibial implant is performed. Typically, the selection of the tibial implant is performed in the process step 124, but may be modified in the process step 140 depending upon how well the selected implant fits with the proximal tibia. As illustrated in FIG. 13, a graphically rendered model of the tibial implant is displayed superimposed over the rendered model of the tibia bone in the navigation panes 202, 204, 206. The positioning of the tibial implant can be adjusted via the selection of a number of implant adjustment buttons. For example, the varus/valgus rotation of the orthopaedic implant may be adjusted via the buttons 240, the superior/inferior or proximal/distal translation of the orthopaedic implant may be adjusted via the buttons 242, the slope of the orthopaedic implant may be adjusted via the buttons 244, the anterior/posterior translation of the orthopaedic implant may be adjust via the buttons 246, the internal/external rotation of the orthopaedic implant may be adjusted by the buttons 248, and the medial/lateral translation of the orthopaedic implant may be adjusted by the buttons 250. Data related to the positioning of the orthopaedic implant is displayed in the surgical step panel 208. Some attributes of the implant, such as the orthopaedic implant size and thickness may be adjusted via the selection of button panels 252 and 254, respectively. Additionally the original location and orientation of the implant may be reset via selection of a reset button 256. Using the various implant adjustment buttons and the implant attribute button panels 252, 254, the surgeon 50 positions and orientates the tibial implant such that a planned resection plane 258 of the tibia bone is determined. Because the surgeon 50 can see a visual rendering of the planned resection plane and the location/orientation of the tibial implant, the surgeon 50 can alter the location and orientation of the resection plane and/or tibial implant until the surgeon 50 is satisfied with the final fitting of the tibial implant to the resected proximal tibia. Once so satisfied, the surgeon 50 may proceed to the next surgical step by selecting the next button select the next button 214.

Figure 14:
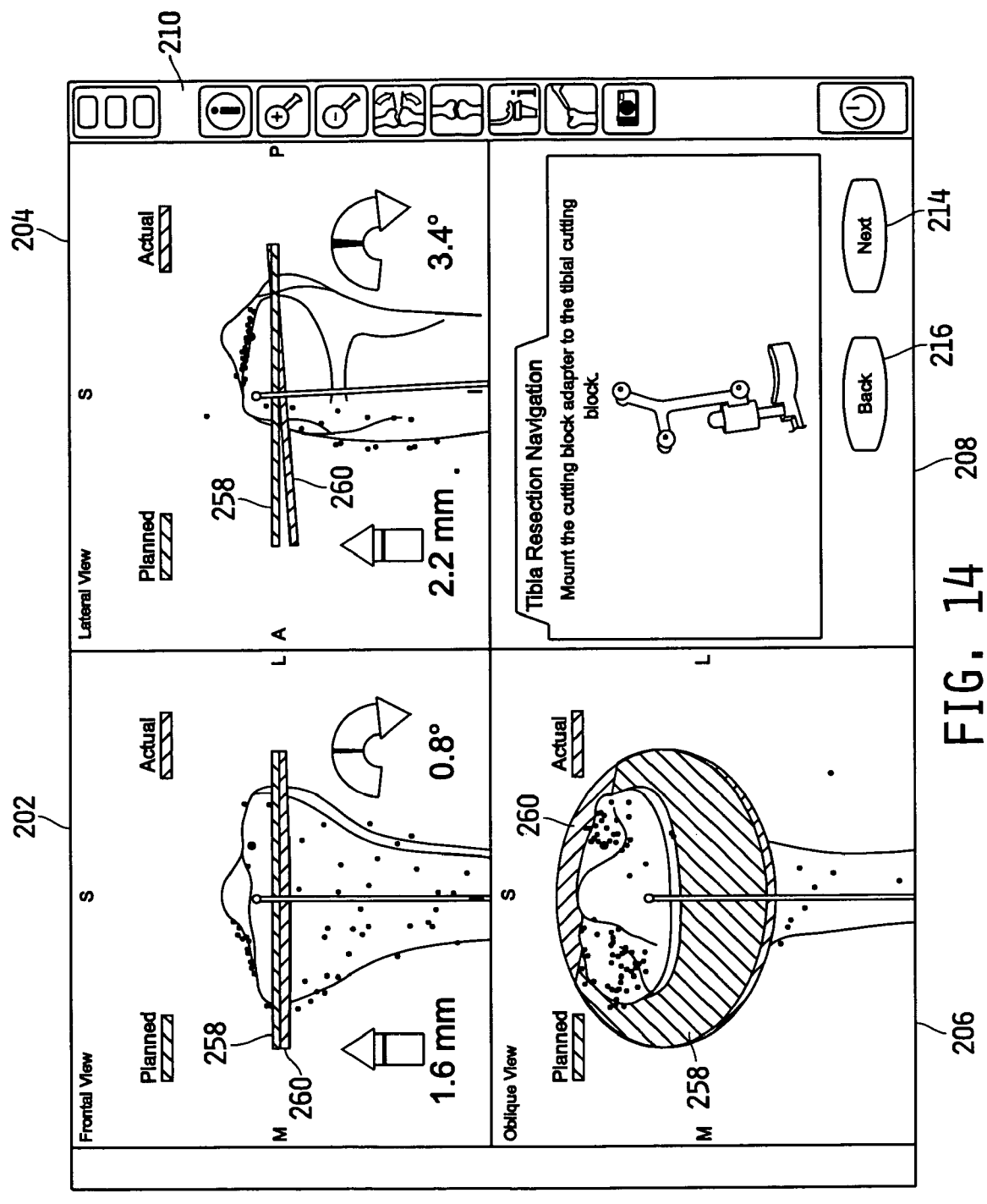

In process step 142 the resectioning of the proximal tibia is planned. To do so, a resection jig, such as the tibial resection jig 90 illustrated in and described above in regard to FIG. 5, is coupled with the tibia bone of the patient 56 near the desired resection location of the proximal tibia. As illustrated in FIG. 14, the computer 12 displays the correct surgical tool to use in the present step in the surgical step pane 208. In response, the computer 12 displays an actual resection plane 260 to the surgeon 50 on the navigation panes 202, 204, 206. As shown, a planned resection plane 258, as determined in step 140, is also displayed. The surgeon 50 may then adjust the coupling of the jig 90 with the tibia bone of the patient 56 such that the actual resection plane 260 overlaps or nearly overlaps the planned resection plane 258. In this way, the surgeon 50 is able to visually monitor the actual resection plane 260 while adjusting the jig 90 such that an accurate resection of the tibia can occur. The surgeon 50 may advance to the next surgical step by selecting the next button 214.

Figure 15:
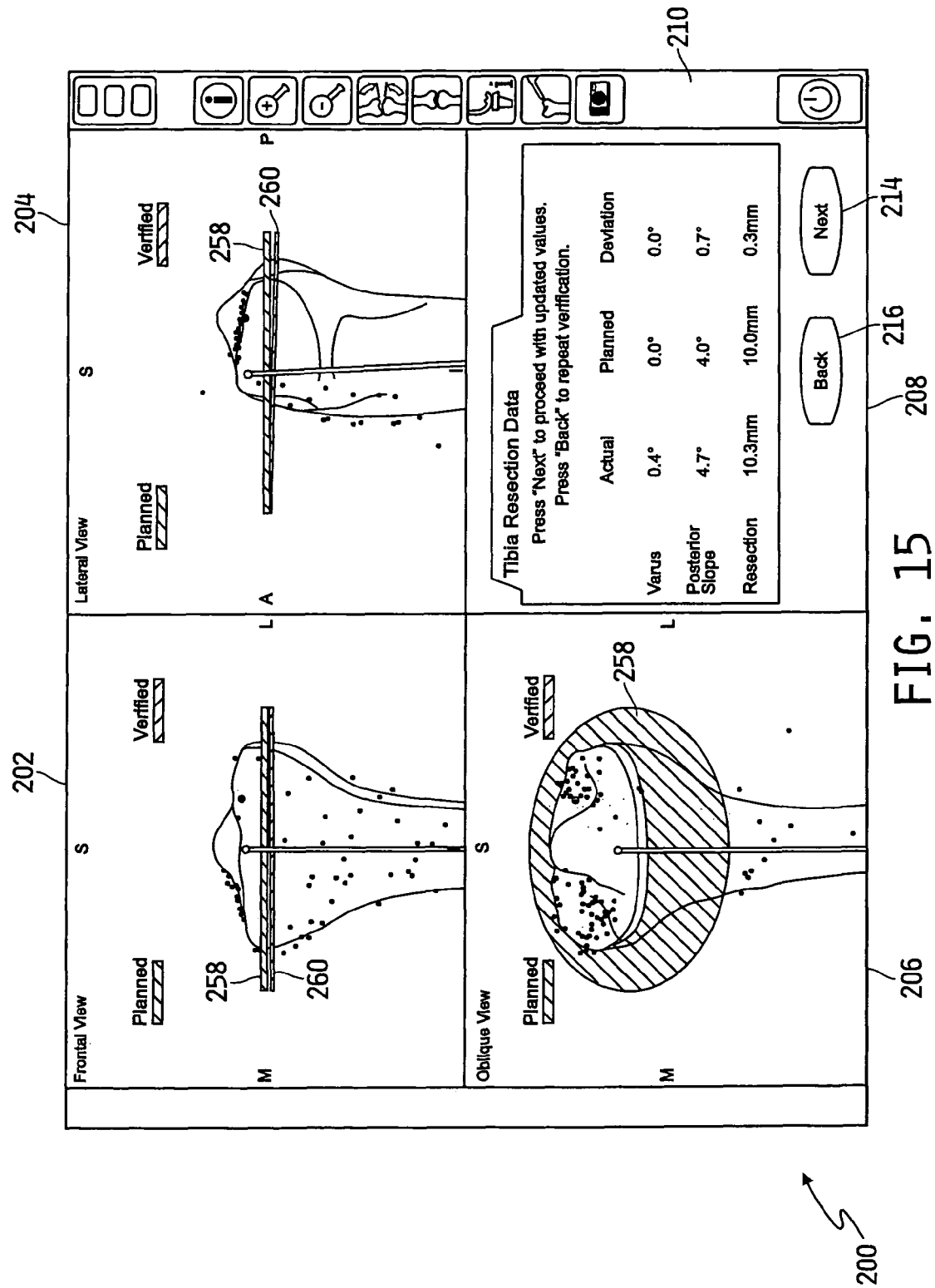

Once the surgeon 50 has reviewed and adjusted the actual resection plane 260 in process step 142, the algorithm 120 advances to process step 144. In process step 144, the tibia is resected using the appropriate resection tool and the jig 90 coupled with the tibia bone of the patient 56. After the proximal tibia has been resected, the computer 12 displays a verified resection plane 262 superimposed with the planned resection plane 258 as illustrated in FIG. 15. The computer 12 also displays data related to the resection of the proximal tibia, including actual, planned, and deviation measurements, in the surgical step panel 208. In this way, the surgeon 50 can compare the final resection of the tibia and the planned resection. If needed, the surgeon 50 can repeat the resectioning process to remove more the proximal tibia. Once the surgeon 50 is satisfied with the resection of the tibia bone, the surgeon 50 may advance to the next surgical step by selecting the next button 214.

Once the tibia bone of the patient 56 has been resected, the relevant distal femur bone is resected in process steps 146-150. In process step 146, the planning for the femoral implant is performed. The femoral implant planning of process step 146 is similar to the tibial implant planning performed in process step 124. During process step 146, the surgeon 50 positions and orients the femoral implant such that a planned resection plane of the distal femur is determined and may also select relevant implant parameters (e.g., size, type, etc.). Because the surgeon 50 can see a visual rendering of the planned resection plane and the location/orientation of the femoral implant, the surgeon 50 can alter the location and orientation of the planned resection plane and/or femoral implant until the surgeon 50 is satisfied with the final fitting of the femoral implant to the resected distal femur.

Once the femoral implant planning is complete, the algorithm 120 advances to process step 148. In process step 148, the resectioning of the distal femur of the patient 56 is planned. The resection planning of the process step 148 is similar to the planning of the tibia resection performed in the process step 142. During the process step 148, a femoral resection jig is coupled with the femur bone of the patient 56. In response, the computer 12 displays an actual resection plane superimposed on the planned resection plane developed in process step 146. By repositioning the femoral resection jig, the surgeon 50 is able to alter the actual resection plane such that an accurate resection of the femur can occur.

Once the surgeon 50 has reviewed and adjusted the actual resection plane of the femur bone, the algorithm 120 advances to process step 150 in which the distal femur is resected using the appropriate resection tool and femoral jig. After the distal femur has been resected, the computer 12 displays a verified resection plane superimposed with the planned resection plane determined in process step 146. In this way, the surgeon 50 can compare the final resection of the femur with the planned resection. Again, if needed, the surgeon 50 can repeat the resectioning process to remove more the distal femur.

Figure 16:
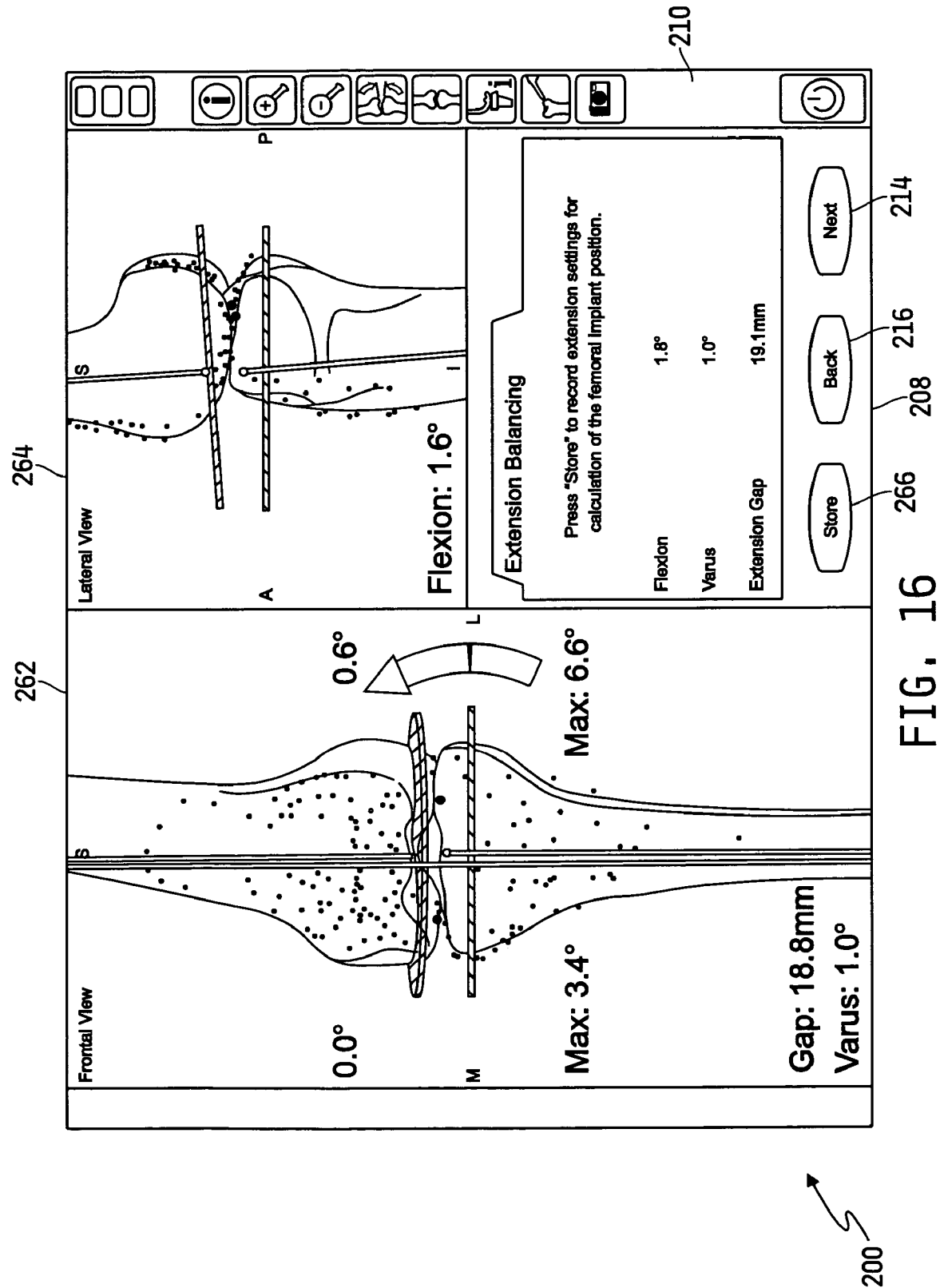

Once the distal femur of the patient 56 has been resected, the algorithm 120 advances to process step 152. In process step 152, ligament balancing of the patient's 56 tibia and femur is performed. Although illustrated as occurring after the resectioning of the tibia and femur bones in FIG. 7, ligament balancing may occur immediately following any resection step (e.g. after the tibia bone is resected) in other embodiments. In process step 152, orthopaedic implant trials (i.e., temporary orthopaedic implants similar to the selected orthopaedic implants) are inserted between the resected ends of the femur and tibia of the patient 56. As illustrated in FIG. 16, the computer 12 displays alignment data of the femur and tibia bone to the surgeon 50 via the display device 44. Specifically, the computer 12 displays a frontal view of the femur bone and tibia bone of the patient 56 in a frontal view pane 262 and a lateral view of the femur and tibia bones in a lateral view pane 264. Each of the panes 262, 264 display alignment data of the femur and tibia bones. Additional alignment data is displayed in the surgical step pane 208. The alignment data may be stored (e.g., in a data storage device included in the computer 20) by selection of a store button 266. The alignment data may subsequently be retrieved and reviewed or used in another procedure at a later time.

Ligament balancing is performed to ensure a generally rectangular shaped extension gap and a generally rectangular shaped flexion gap at a predetermined joint force value has been established between the patient's 56 proximal tibia and the distal femur. To do so, a ligament balancer may be used to measure the medial and lateral joint forces and the medial and lateral gap distances when the patient's 56 leg is in extension (i.e., the patient's 56 tibia is positioned at about 0 degrees relative to the patient's femur) and in flexion (i.e., the patient's 56 tibia is positioned at about 90 degrees relative to the patient's femur). An exemplary ligament balancer that may be used to perform these measurements is described in U.S. patent application Ser. No. 11/094,956, which issued as U.S. Pat. No. 7,615,055 and was filed on Mar. 31, 2005, the entirety of which is expressly incorporated herein by reference. In either extension or flexion, if the medial and lateral gap distances are not approximately equal (i.e., do not form a generally rectangular shaped joint gap) at the predetermined joint force value, ligament release (i.e., cutting of a ligament) may be performed to equalize the medial and/or lateral gap distances. Additionally or alternatively, the orthopaedic implant trial may be replaced with an alternative implant trial. In this way, the surgeon 50 ensures an accurate alignment of the tibia bone and femur bone of the patient 56.

Figure 17:
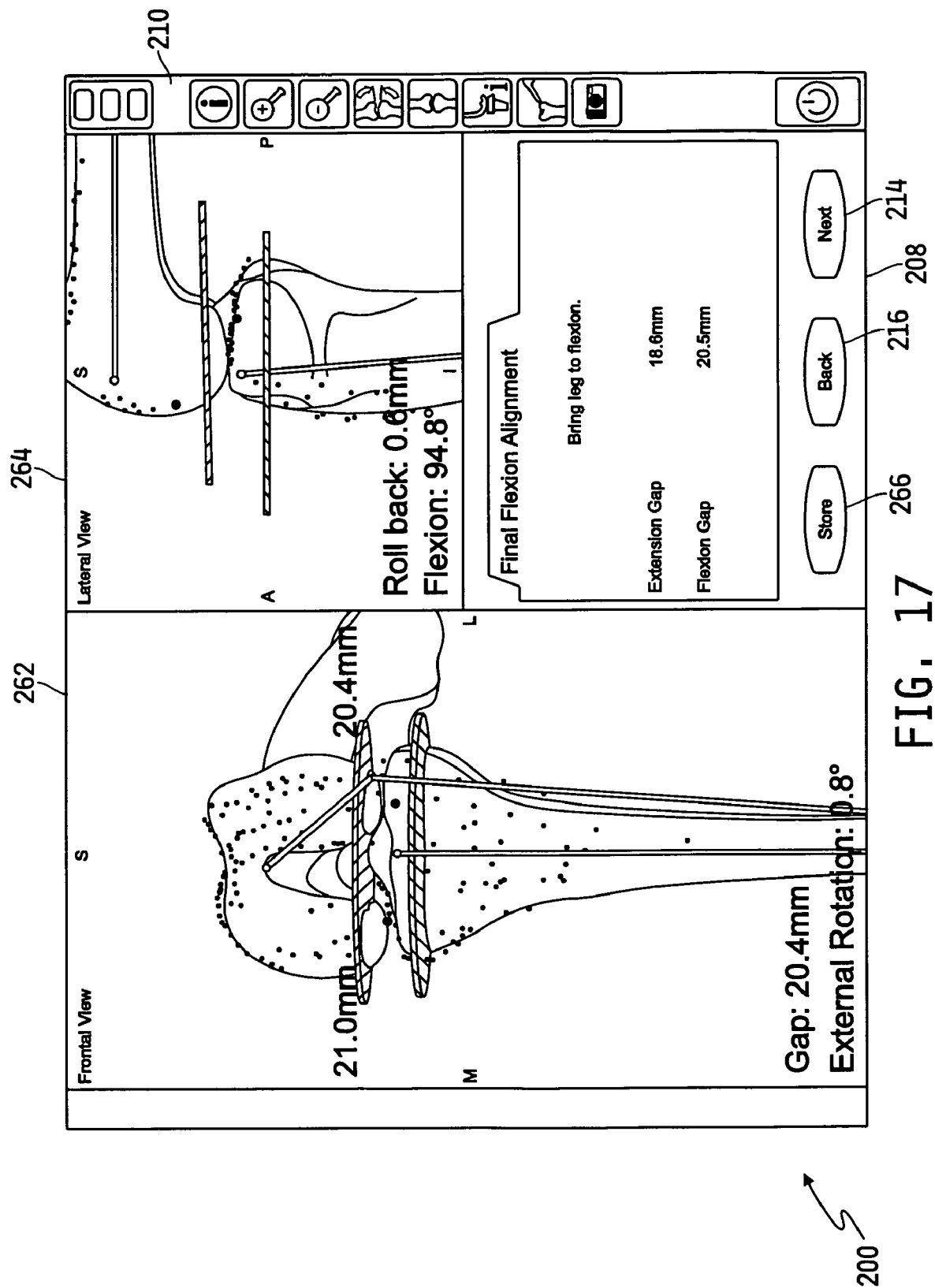

Once any desired ligament balancing is completed in process step 15, the algorithm 120 advances to process step 154 in which a final verification of the orthopaedic implants is performed. In process step 154, the orthopaedic implants are coupled with the distal femur and proximal tibia of the patient 56 and the alignment of the femur and tibia bones are verified in flexion and extension. To do so, the computer 12 displays the rendered images of the femur bone and tibia bone and alignment data to the surgeon 50 via the display device 44, as illustrated in FIG. 17. As indicated in the surgical step pane 208, the surgeon 50 is instructed to move the patient's 56 leg to flexion and extension such that the overall alignment can be determined and reviewed. If the femur and tibia bones of the patent 56 are not aligning (i.e., the flexion and/or extension gap is non-rectangular) to the satisfaction of the surgeon 50, the surgeon may perform additional ligament balancing as discussed above in regard to process step 152. Once the surgeon 50 has verified the final alignment of the femur and tibia bones (i.e., the flexion and extension gaps), the surgeon 50 may store the final alignment data via selecting the store button 266. The surgeon 50 may subsequently complete the orthopaedic surgical procedure by selecting the next button 214.

Figure 18:
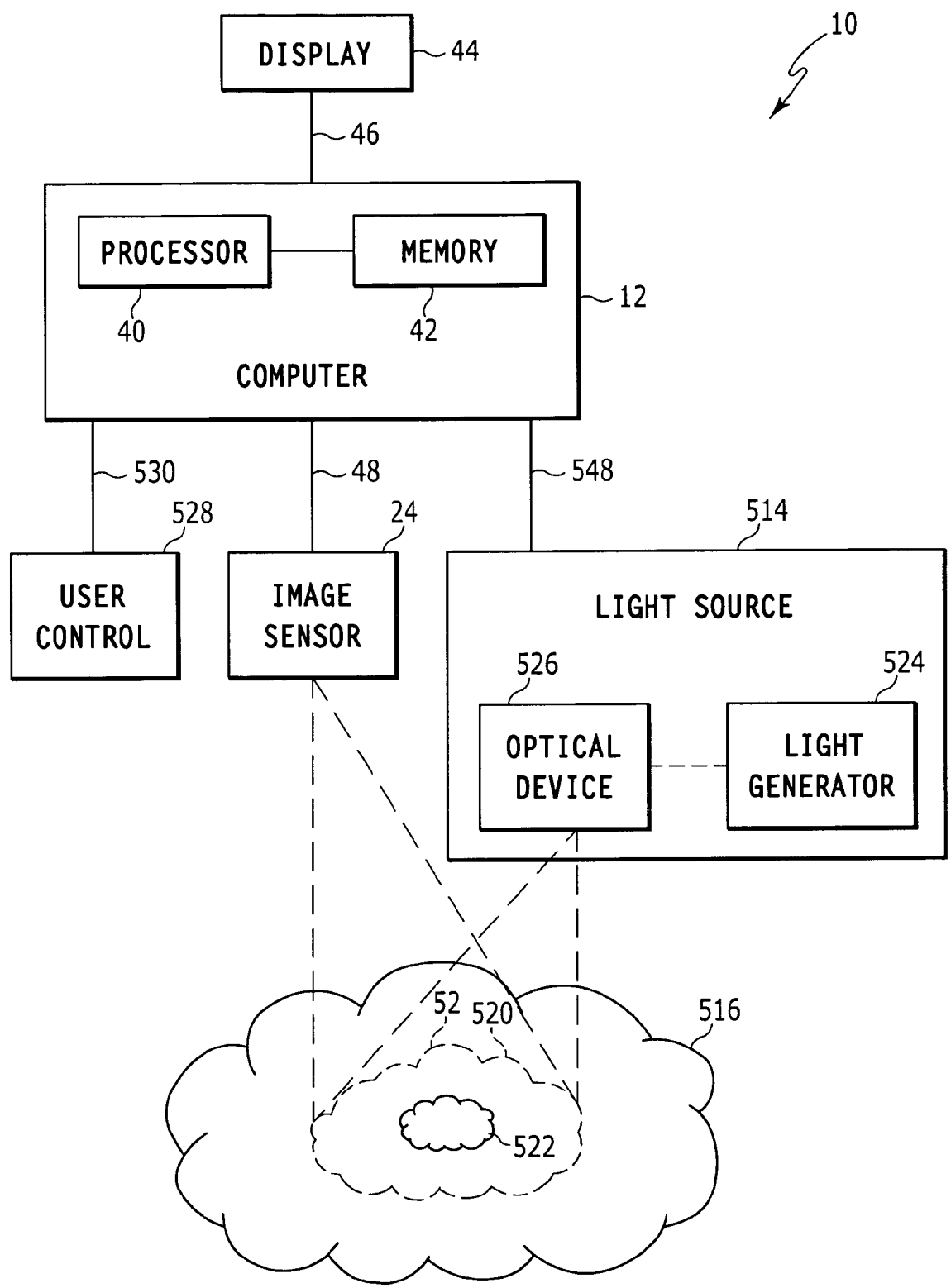
FIG. 18 is a simplified diagram of another embodiment of a CAOS system having a light source for use with an image sensor of the CAOS system.

Referring to FIG. 18, there is shown an embodiment of the CAOS system 10 comprising the image sensor 24 and a light source 514. The image sensor 24 is configured to sense an image of an area 516 associated with an orthopaedic surgical site. Further, the image sensor 24 has a field of view 52. The light source 514 is secured to the image sensor 24 to project light (e.g., focused light) distinct from any ambient lighting onto the area 516 in a pattern 520 visually indicative of at least a portion of the field of view 52. What is meant herein by "ambient lighting" is any natural or artificial white light present in the surgical area, including white task lighting that may be projected onto the area 516. Examples of such artificial lighting include room lighting (e.g., ceiling lighting, wall lighting), surgical and/or examination lighting (e.g., repositionable lighting typically brighter than the room lighting), and the like.

Such an arrangement facilitates repositioning of the image sensor 24 so that a desired portion 522 of the area 516 can be placed within the field of view 52 for display by the display 44 in a relatively quick and efficient manner. Indeed, the image sensor 24 may be repositionable and the light source 514 may be secured to the image sensor 24 for movement therewith in a fixed orientation relative thereto such that the light source 514 remains aligned relative to the image sensor 24 upon repositioning of the image sensor 24. As such, the light source 514 is arranged relative to the image sensor 24 such that the pattern of light 520 moves with the field of view 52 in alignment therewith upon movement of the field of view 52. Stated otherwise, the position of the pattern of light 520 depends on the position of the field of view 52.

The light pattern 520 projected by the light source 514 may or may not be coterminous with the field of view 52. For example, in FIG. 18, the light pattern 520 is shown as being coterminous with the field of view 52. However, in other examples, the light pattern 520 may be somewhat smaller or larger than the field of view 52 but nonetheless indicative of the field of view 52.

Illustratively, the light source 514 projects light onto the area 516 in a linear pattern. The linear pattern may take the form of a wide variety of shapes and sizes including, but not limited to, a circle (FIG. 19), a rectangle (FIG. 20), a triangle a polygon, any other geometric shape, or an irregular shape, to name just a few. The lines of the linear pattern may be continuous or broken (e.g., dashed or dotted lines). The image sensor 24 may thus be repositioned so that the desired portion 522 of the area 516 is within the boundaries of the linear pattern to thereby indicate to a user of the CAOS system 10 that the desired portion 522 is within the field of view 52.

Exemplarily, the light source 514 includes a light generator 524 for generating the light projected therefrom onto the area 516. The light generator 524 may be configured, for example, as a laser or a laser diode. In some examples, a laser pointer or laser pen may be used as the light generator 524. In other examples, incandescent or fluorescent lighting may be used as the light generator 524. The color of the light generated by the light generator 524 may be white or non-white (e.g., green, red). A non-white color would be useful for distinguishing the light generated by the light generator 524 from room lighting or other lighting.

An optical device 526 may be used to modify the light generated by the light generator 524 into the desired pattern 520. The optical device 526 may include, but is not limited to, diffractive optics, lenses, mirrors, fiber optics, and the like. It is within the scope of this disclosure to configure the optical device 526 to offer the user a plurality of light patterns from which to choose, each light pattern being indicative of the field of view 52. As such, the optical device 526 may include a pattern selector operable by the user (possibly through an input device of the computer 12 or other mechanism) to selectively employ one of the light patterns from among the plurality of light patterns. Exemplarily, the pattern selector may include a plurality of end caps for modifying the generated light into different shapes and/or symbols. The image sensor 24 may have a zoom feature for selectively zooming in or out. In such a case, the optical device 526 may be coordinated with the zoom feature of the sensor 24 to adjust the size of the pattern 520 accordingly in response to adjustment of the sensor's zoom feature.

The image sensor 24 and the light source 514 are under the control of the computer 12 (which may be referred to as a controller). Specifically, the computer 12 is electrically coupled to the image sensor 24 via a communication link 48 to operate the image sensor 24 and electrically coupled to the light source 514 via a communication link 548 to operate the light source 514. The computer 12 is also electrically coupled to a user control 528 via a communication link 530 so as to be responsive to operation of the user control 528 to cause operation of the light source 514.

The light source 514 may be used with a variety of image sensors 24. For example, the image sensor 24 may be a stereoscopic camera head having two cameras arranged in stereoscopic relation or it may have only a single camera.

Figure 19:
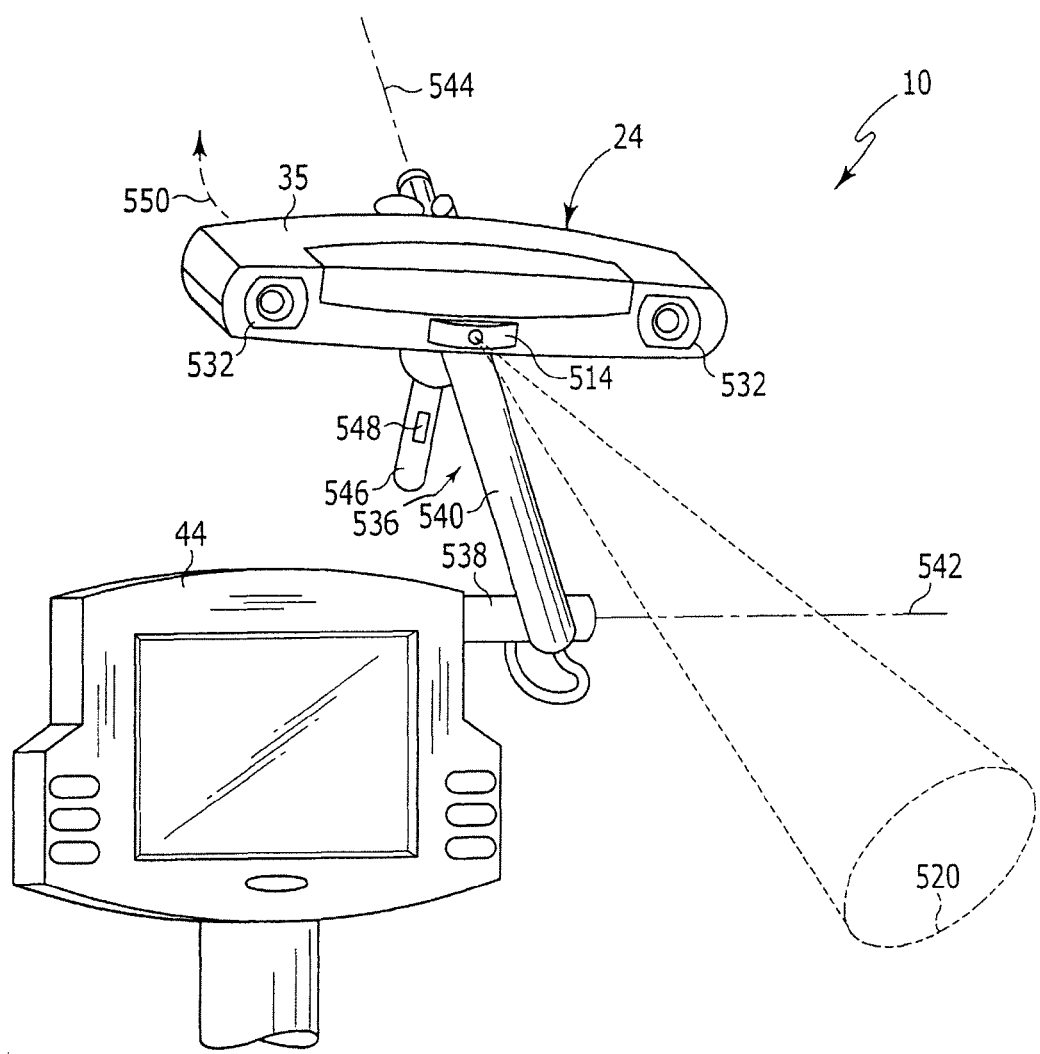
FIGS. 19-21 are perspective views of an example of the image sensor and light source of the CAOS system of FIG. 18.
Figure 20:
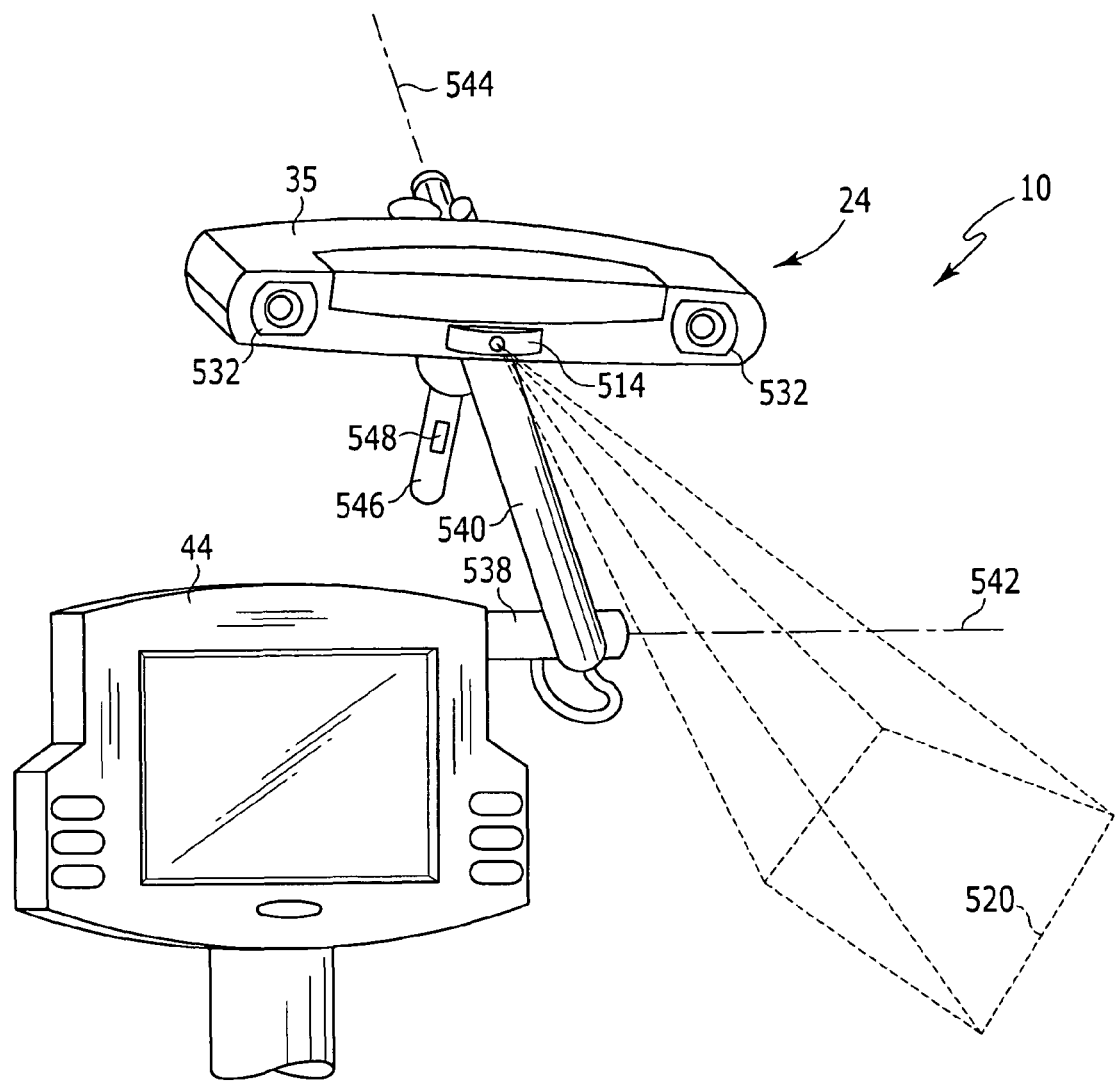
Figure 21:
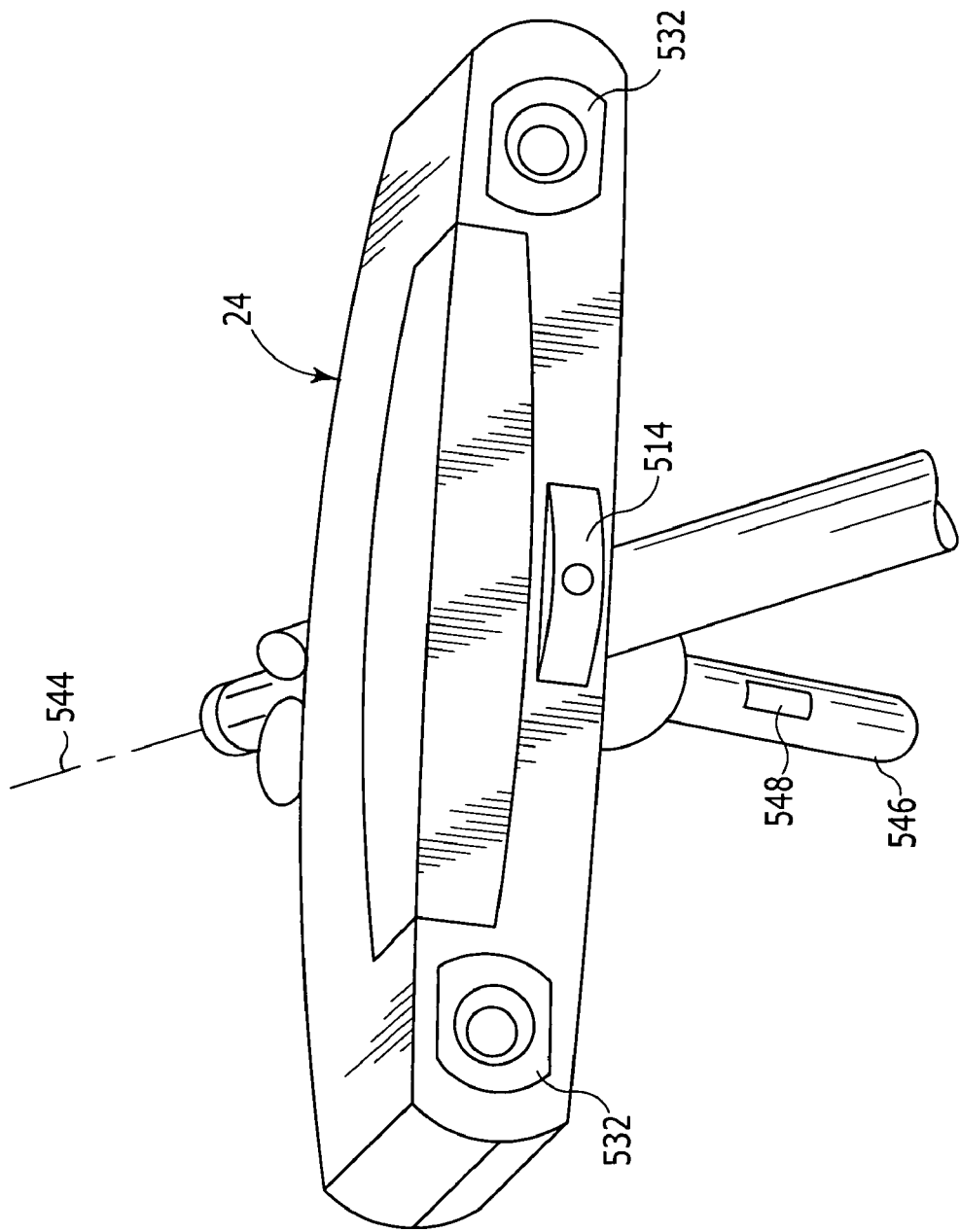

Referring to FIGS. 19-21, there is shown an embodiment of the CAOS system 10. The image sensor 24 is configured, for example, as a stereoscopic camera head having two cameras 532 secured to a housing 35 of the camera head. The light source 514 is secured to and embedded in the housing 35 at a location between the two cameras 532 in generally fixed relation thereto. As such, the housing 35 and any other mechanical components helping to secure the light source 514 to the image sensor 24 act as a movement coordinator so that the light pattern 520 moves with the field of view 52 in alignment therewith upon movement of the field of view 52. Other movement coordinators are within the scope of this disclosure. For example, there may be one or more sensor(s) for sensing movement of the image sensor 24 and thus movement of the field of view 52. The controller 12 may, upon receipt of signals indicative of such movement, operate a device (e.g., motor and any associated drive elements) to cause coordinated movement of the light pattern 520 with the field of view 52.

The light pattern 520 projected by the light source 514 is shown as being circular in FIG. 19 and rectangular in FIG. 20 but may take a variety of shapes and sizes as alluded to above.

In the exemplary embodiment of FIGS. 19-21, the camera head 24 and light source 514 secured thereto are secured to a support 536. Illustratively, the support 536 includes a first bar 538 secured to the display or base 44 and a second bar 540 secured to the first bar 538 and the camera head 24 for rotation of the head 24 and light source 514 about an axis 542 defined by the first bar 538. The camera head 24 is secured to the second bar 540 for rotation about an axis 544.

A handle 546 secured to the head housing 35 can be manipulated by a user to reposition the camera head 24 and light source 514 relative to the base 44. To do so, the user grips the handle 546 and operates a user control 548 secured thereto. Such operation of the user control 548 unlocks the head 24 and light source 514 for movement relative to the base 44. The computer 12 detects such unlocking and operates the light source 514 to cause generation of light thereby in response to detection of the unlocking of the head 24 and light source 514. Thus, operation of the user control 548 simultaneously causes the computer 12 to operate the light source 514 to provide the user a visual indication of the field of view 52.

Figure 22B:
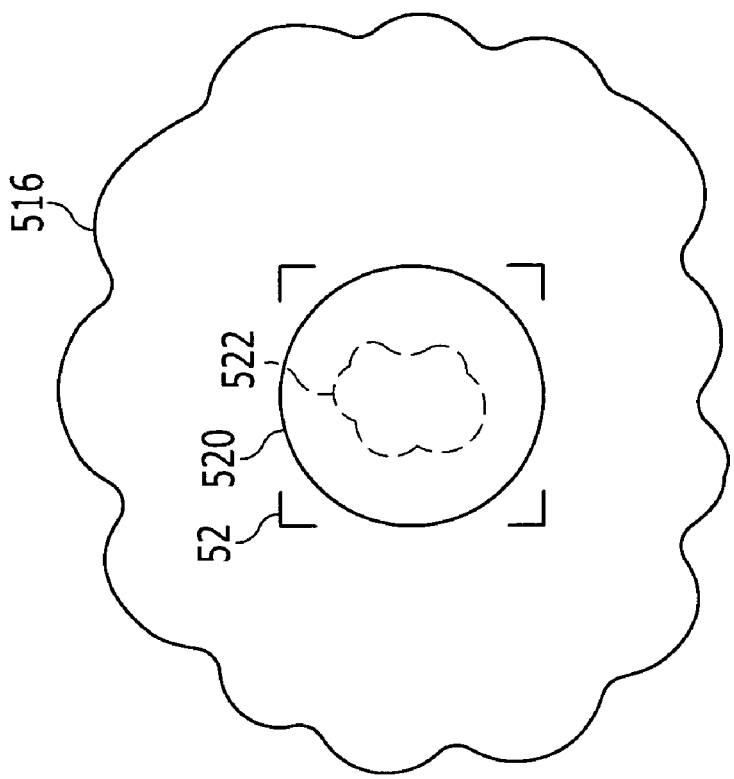
FIG. 22b is a simplified diagram similar to FIG. 22a showing the desired portion of the area now inside the field of view.
Figure 22A:
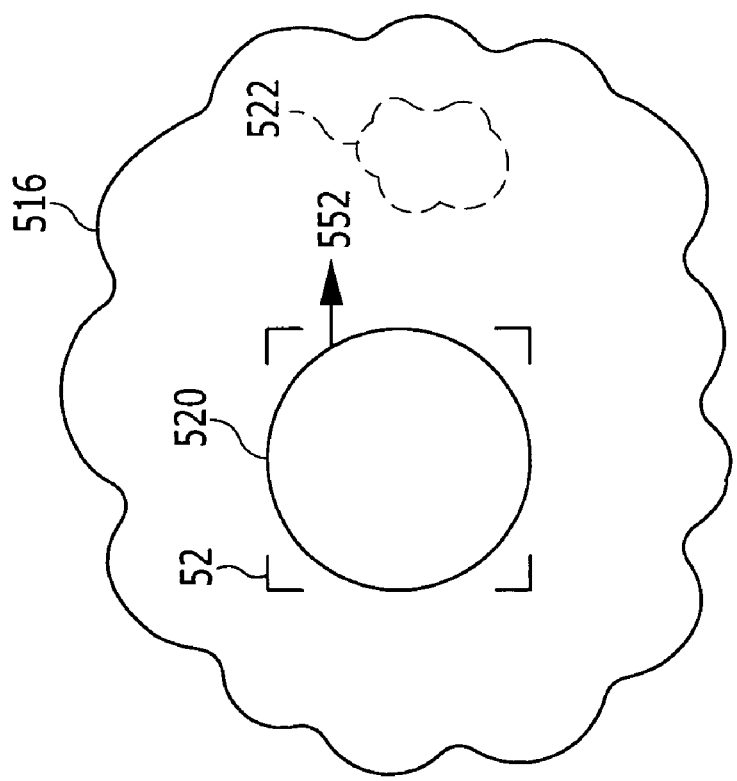
FIG. 22a is a simplified diagram showing a desired portion of an area of an orthopaedic surgical site outside of the field of view of the image sensor as indicated by the circular light pattern projected by light source.

In this way, a user can reposition the camera 24 and indicator 516 in a variety of directions such as, for example, direction 550 (FIG. 19) to move the field of view 52 and light pattern 520 from a position shown, for example, in FIG. 22a in a direction 552 to a position shown, for example, in FIG. 22b in which the desired portion 522 of the area 516 is within the field of view 52. In this example, the light pattern 520 is not coterminous with the field of view 52 as suggested by the circular light pattern 520 within the generally square field of view 52 in FIGS. 22a and 22b. However, as alluded to above, the light pattern 520 may or may not be coterminous with the field of view 52. Further, the circular shape of the field of view 52 and light pattern 520 shown in FIGS. 22a and 22b is shown merely as one example of the many different shapes and sizes possible for the field of view 58 and light pattern 520.

Release of the handle 546 causes the head 24 and light source 514 to be relocked in place and causes the computer 12 to deactivate the light source 514 to cease generation of light by the light generator 524. The user control 548 may be, for example, a pressure-sensitive switch embedded in the grip portion of the handle 546.

Illustratively, the display is included in the base 44. However, it is to be understood that the base 44 may be configured in many different ways that may or may not include the display. For example, the base 44 may take the form of the base 22. In other examples, the base 44 may be embodied as an attachment to the floor, wall, ceiling, or other structure and may be fixed or movable relative thereto.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A method of operating a computer assisted orthopaedic surgery system, the method comprising:
   detecting an unlocking of an image sensor for movement relative to a base to which the image sensor is secured, and projecting light from a light source distinct from any ambient lighting onto an area associated with an orthopaedic surgical site in a pattern visually indicative of a field of view of the image sensor configured to sense an image of the area, wherein the pattern is coterminous with the field of view of the image sensor, wherein projecting light comprises operating the light source in response to detection of the unlocking of the image sensor.

2. The method of claim 1, wherein projecting light comprises projecting the light onto the area in a linear pattern.

3. The method of claim 2, wherein projecting light comprises (i) emitting light from a light generator and (ii) modifying the emitted light into the linear pattern with an optical device.

4. The method of claim 1, wherein projecting light comprises operating a laser or a laser diode.

5. The method of claim 1, further comprising moving the image sensor, wherein projecting light comprises generating the light during movement of the image sensor.

6. A computer assisted orthopaedic surgery system, comprising:
    a base,
    an image sensor moveably coupled to the base, the image sensor being configured to sense an image of an area associated with an orthopaedic surgical site, the image sensor having a field of view,
    a user control configured to unlock the image sensor for movement relative to the base
    a light source to project light distinct from any ambient lighting onto the area in a pattern coterminous with the field of view, and
    a controller electrically coupled to the image sensor and the light source, the controller comprising (i) a processor, and (ii) a memory device electrically coupled to the processor, the memory device having stored therein a plurality of instructions which, when executed by the processor, cause the processor to:
    detect an unlocking of the image sensor for movement relative to the base, and
    operate the light source to project light distinct from any ambient lighting onto the area in the pattern so as to visually indicate the field of view of the image sensor in response to detection of the unlocking of the image sensor.

7. The computer assisted orthopaedic surgery system of claim 6, wherein:
    the image sensor comprises a stereoscopic camera head, and
    the plurality of instructions, when executed by the processor, cause the processor to operate the light source so as to generate a visual indication of the field of view of the stereoscopic camera head.

8. The computer assisted orthopaedic surgery system of claim 6, further comprising a second user control electrically coupled to the controller, wherein the plurality of instructions, when executed by the processor, cause the processor to operate the light source in response to operation of the second user control.

9. The computer assisted orthopaedic surgery system of claim 6, wherein the light source is secured to the image sensor for movement therewith in a fixed orientation relative thereto upon repositioning of the image sensor.

10. The computer assisted orthopaedic surgery system of claim 6, wherein the light source is arranged relative to the image sensor such that the pattern of light moves with the field of view in alignment therewith upon movement of the field of view.

11. A computer assisted orthopaedic surgery system, comprising:
    a base,
    an image sensor moveably coupled to the base, the image sensor being configured to sense an image of an area associated with an orthopaedic surgical site, the image sensor having a field of view,
    a light source secured to the image sensor to project light distinct from any ambient lighting onto the area in a pattern coterminous with the field of view, the pattern providing a visual indication of the field of view on the area associated with the orthopaedic surgical site,
    a user control configured to unlock the image sensor for movement relative to the base, and
    a processor configured to operate the light source in response to an unlocking of the image sensor for movement relative to the base.

12. The computer assisted orthopaedic surgery system of claim 11, wherein:
    the light source is secured to the image sensor for movement therewith in a fixed orientation relative thereto such that the light source remains aligned relative to the image sensor upon movement of the image sensor.

13. The computer assisted orthopaedic surgery system of claim 11, wherein the light source is configured to project a linear pattern of light onto the area.

14. The computer assisted orthopaedic surgery system of claim 11, wherein the light source comprises a laser or a laser diode.

15. The computer assisted orthopaedic surgery system of claim 11, wherein the light source comprises an optical device configured to modify the light generated by the light source into the pattern.

16. The computer assisted orthopaedic surgery system of claim 11, wherein the image sensor comprises a first camera.

17. The computer assisted orthopaedic surgery system of claim 16, wherein:
    the image sensor comprises a second camera positioned in stereoscopic relation to the first camera, and
    the light source is located between the first camera and the second camera.

18. The computer assisted orthopaedic surgery system of claim 16, wherein the image sensor comprises a housing to which the first camera and the light source are secured.

19. The computer assisted orthopaedic surgery system of claim 11, further comprising (i) a second user control for operating the light source, and (ii) a handle secured to the second user control.

20. The computer assisted orthopaedic surgery system of claim 11, wherein the light source is arranged relative to the image sensor such that the position of the pattern of light depends on the position of the field of view.

* * * * *